US008287477B1

(12) United States Patent
Herr et al.

(10) Patent No.: US 8,287,477 B1
(45) Date of Patent: Oct. 16, 2012

(54) ACTIVE ANKLE FOOT ORTHOSIS

(75) Inventors: Hugh Herr, Somerville, MA (US); Joaquin Blaya, Miami, FL (US); Gill A. Pratt, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 13/363,993

(22) Filed: Feb. 1, 2012

Related U.S. Application Data

(63) Continuation of application No. 13/299,953, filed on Nov. 18, 2011, which is a continuation of application No. 10/671,329, filed on Sep. 25, 2003, now Pat. No. 8,075,633.

(51) Int. Cl.
*A61F 5/00* (2006.01)
(52) U.S. Cl. .................. 602/16; 602/23; 602/27
(58) Field of Classification Search .......... 602/16, 602/23, 26–27; 128/882; 74/490.01, 490.1
See application file for complete search history.

(56) References Cited

U.S. PATENT DOCUMENTS

| 2,489,291 | A | 11/1949 | Henschke et al. |
| 2,529,968 | A | 11/1950 | Sartin |
| 3,098,645 | A | 7/1963 | Owens |
| 3,207,497 | A | 9/1965 | Schoonover |
| 3,844,279 | A | 10/1974 | Konvalin |
| 4,442,390 | A | 4/1984 | Davis |
| 4,463,291 | A | 7/1984 | Usry |
| 4,518,307 | A | 5/1985 | Bloch |
| 4,532,462 | A | 7/1985 | Washbourn et al. |
| 4,546,295 | A | 10/1985 | Wickham et al. |
| 4,546,296 | A | 10/1985 | Washbourn et al. |
| 4,546,297 | A | 10/1985 | Washbourn et al. |
| 4,546,298 | A | 10/1985 | Wickham et al. |
| 4,569,352 | A | 2/1986 | Petrofsky et al. |
| 4,600,357 | A | 7/1986 | Coules |

(Continued)

FOREIGN PATENT DOCUMENTS

EP     1393866 A1     3/2004

(Continued)

OTHER PUBLICATIONS

Blaya, J.A., "Force-Controllable Ankle Foot Orthosis (AFO) to Assist Drop Foot Gait," submitted to the Department of Mechanical Engineering, Massachusetts Institute of Technology, Cambridge, Massachusetts (Feb. 2003). 88 pages.

(Continued)

*Primary Examiner* — Michael A. Brown
(74) *Attorney, Agent, or Firm* — Goodwin Procter LLP

(57) ABSTRACT

An Active Ankle Foot Orthosis (AAFO) is provided where the impedance of an orthotic joint is modulated throughout the walking cycle to treat ankle foot gait pathology, such as drop foot gait. During controlled plantar flexion, a biomimetic torsional spring control is applied where orthotic joint stiffness is actively adjusted to minimize forefoot collisions with the ground. Throughout late stance, joint impedance is minimized so as not to impede powered plantar flexion movements, and during the swing phase, a torsional spring-damper (PD) control lifts the foot to provide toe clearance. To assess the clinical effects of variable-impedance control, kinetic and kinematic gait data were collected on two drop foot participants wearing the AAFO. It has been found that actively adjusting joint impedance reduces the occurrence of slap foot, allows greater powered plantar flexion, and provides for less kinematic difference during swing when compared to normals.

24 Claims, 7 Drawing Sheets

U.S. PATENT DOCUMENTS

| | | |
|---|---|---|
| 4,657,470 A | 4/1987 | Clarke et al. |
| 4,843,921 A | 7/1989 | Kremer |
| 4,865,376 A | 9/1989 | Leaver et al. |
| 4,872,803 A | 10/1989 | Asakawa |
| 4,909,535 A | 3/1990 | Clark et al. |
| 4,921,293 A | 5/1990 | Ruoff et al. |
| 4,921,393 A | 5/1990 | Andeen et al. |
| 4,923,474 A | 5/1990 | Klasson et al. |
| 4,923,475 A | 5/1990 | Gosthnian et al. |
| 4,964,402 A | 10/1990 | Grim et al. |
| 4,989,161 A | 1/1991 | Oaki |
| 5,012,591 A | 5/1991 | Asakawa |
| 5,049,797 A | 9/1991 | Phillips |
| 5,062,673 A | 11/1991 | Mimura |
| 5,088,478 A | 2/1992 | Grim |
| 5,092,902 A | 3/1992 | Adams et al. |
| 5,112,296 A | 5/1992 | Beard et al. |
| 5,174,168 A | 12/1992 | Takagi et al. |
| 5,181,933 A | 1/1993 | Phillips |
| 5,252,102 A | 10/1993 | Singer et al. |
| 5,294,873 A | 3/1994 | Seraji |
| RE34,661 E | 7/1994 | Grim |
| 5,327,790 A | 7/1994 | Levin et al. |
| 5,367,790 A | 11/1994 | Gamow et al. |
| 5,383,939 A | 1/1995 | James |
| 5,405,409 A | 4/1995 | Knoth |
| 5,442,270 A | 8/1995 | Tetsuaki |
| 5,443,521 A | 8/1995 | Knoth et al. |
| 5,456,341 A | 10/1995 | Garnjost et al. |
| 5,458,143 A | 10/1995 | Herr |
| 5,476,441 A | 12/1995 | Durfee et al. |
| 5,502,363 A | 3/1996 | Tasch et al. |
| 5,514,185 A | 5/1996 | Phillips |
| 5,556,422 A | 9/1996 | Powell, III et al. |
| 5,571,205 A | 11/1996 | James |
| 5,643,332 A | 7/1997 | Stein |
| 5,650,704 A | 7/1997 | Pratt et al. |
| 5,662,693 A | 9/1997 | Johnson et al. |
| 5,701,686 A | 12/1997 | Herr et al. |
| 5,718,925 A | 2/1998 | Kristinsson et al. |
| 5,748,845 A | 5/1998 | Labun et al. |
| 5,776,205 A | 7/1998 | Phillips |
| 5,885,809 A | 3/1999 | Effenberger et al. |
| 5,888,212 A | 3/1999 | Petrofsky et al. |
| 5,898,948 A | 5/1999 | Kelly et al. |
| 5,910,720 A | 6/1999 | Williamson et al. |
| 5,932,230 A | 8/1999 | DeGrate |
| 5,971,729 A | 10/1999 | Kristinsson et al. |
| 5,972,036 A | 10/1999 | Kristinsson et al. |
| 5,980,435 A | 11/1999 | Joutras et al. |
| 6,029,374 A | 2/2000 | Herr et al. |
| 6,056,712 A | 5/2000 | Grim |
| 6,067,892 A | 5/2000 | Erickson |
| 6,071,313 A | 6/2000 | Phillips |
| 6,136,039 A | 10/2000 | Kristinsson et al. |
| 6,144,385 A | 11/2000 | Girard |
| 6,202,806 B1 | 3/2001 | Sandrin et al. |
| 6,223,648 B1 | 5/2001 | Erickson |
| 6,240,797 B1 | 6/2001 | Morishima et al. |
| 6,267,742 B1 | 7/2001 | Krivosha et al. |
| 6,416,703 B1 | 7/2002 | Kristinsson et al. |
| 6,443,993 B1 | 9/2002 | Koniuk |
| 6,456,884 B1 | 9/2002 | Kenney |
| 6,478,826 B1 | 11/2002 | Phillips et al. |
| 6,485,776 B2 | 11/2002 | Janusson et al. |
| 6,507,757 B1 | 1/2003 | Swain et al. |
| 6,511,512 B2 | 1/2003 | Phillips et al. |
| 6,517,503 B1 | 2/2003 | Naft et al. |
| 6,589,289 B2 | 7/2003 | Ingimarsson |
| 6,592,539 B1 | 7/2003 | Einarsson et al. |
| 6,610,101 B2 | 8/2003 | Herr et al. |
| 6,626,952 B2 | 9/2003 | Janusson et al. |
| 6,666,796 B1 | 12/2003 | MacCready, Jr. |
| 6,706,364 B2 | 3/2004 | Janusson et al. |
| 6,752,774 B2 | 6/2004 | Townsend et al. |
| 6,764,520 B2 | 7/2004 | Deffenbaugh et al. |
| 6,811,571 B1 | 11/2004 | Phillips |
| D503,480 S | 3/2005 | Ingimundarson et al. |
| D503,802 S | 4/2005 | Bjarnason |
| 6,887,279 B2 | 5/2005 | Phillips et al. |
| 6,923,834 B2 | 8/2005 | Karason |
| 6,936,073 B2 | 8/2005 | Karason |
| 6,945,947 B2 | 9/2005 | Ingimundarson et al. |
| 6,966,882 B2 | 11/2005 | Horst |
| 6,969,408 B2 | 11/2005 | Lecomte et al. |
| 7,001,563 B2 | 2/2006 | Janusson et al. |
| 7,025,793 B2 | 4/2006 | Egilsson |
| 7,029,500 B2 | 4/2006 | Martin |
| 7,037,283 B2 | 5/2006 | Karason et al. |
| D523,149 S | 6/2006 | Bjarnason |
| 7,063,727 B2 | 6/2006 | Phillips et al. |
| 7,077,818 B2 | 7/2006 | Ingimundarson et al. |
| 7,094,058 B2 | 8/2006 | Einarsson |
| 7,094,212 B2 | 8/2006 | Karason et al. |
| D527,825 S | 9/2006 | Ingimundarson et al. |
| D529,180 S | 9/2006 | Ingimundarson et al. |
| 7,101,487 B2 | 9/2006 | Hsu et al. |
| 7,105,122 B2 | 9/2006 | Karason |
| 7,107,180 B2 | 9/2006 | Karason |
| 7,118,601 B2 | 10/2006 | Yasui et al. |
| 7,118,602 B2 | 10/2006 | Bjarnason |
| 7,136,722 B2 | 11/2006 | Nakamura et al. |
| D533,280 S | 12/2006 | Wyatt et al. |
| 7,144,429 B2 | 12/2006 | Carstens |
| 7,145,305 B2 | 12/2006 | Takenaka et al. |
| 7,154,017 B2 | 12/2006 | Sigurjonsson et al. |
| 7,161,056 B2 | 1/2007 | Gudnason et al. |
| 7,169,188 B2 | 1/2007 | Carstens |
| 7,169,189 B2 | 1/2007 | Bjarnason et al. |
| 7,169,190 B2 | 1/2007 | Phillips et al. |
| 7,198,071 B2 | 4/2007 | Bisbee, III et al. |
| 7,198,610 B2 | 4/2007 | Ingimundarson et al. |
| 7,217,060 B2 | 5/2007 | Ingimarsson |
| 7,220,889 B2 | 5/2007 | Sigurjonsson et al. |
| 7,223,899 B2 | 5/2007 | Sigurjonsson |
| 7,227,050 B2 | 6/2007 | Sigurjonsson et al. |
| 7,230,154 B2 | 6/2007 | Sigurjonsson |
| 7,235,108 B2 | 6/2007 | Carstens |
| 7,240,876 B2 | 7/2007 | Doubleday et al. |
| 7,266,910 B2 | 9/2007 | Ingimundarson |
| 7,270,644 B2 | 9/2007 | Ingimundarson |
| 7,279,009 B2 | 10/2007 | Herr et al. |
| 7,288,076 B2 | 10/2007 | Grim et al. |
| 7,295,892 B2 | 11/2007 | Herr et al. |
| RE39,961 E | 12/2007 | Petrofsky et al. |
| 7,303,538 B2 | 12/2007 | Grim et al. |
| 7,304,202 B2 | 12/2007 | Sigurjonsson et al. |
| 7,311,686 B1 | 12/2007 | Iglesias et al. |
| 7,313,463 B2 | 12/2007 | Herr et al. |
| D558,884 S | 1/2008 | Ingimundarson et al. |
| 7,335,233 B2 | 2/2008 | Hsu et al. |
| 7,347,877 B2 | 3/2008 | Clausen et al. |
| D567,072 S | 4/2008 | Ingimundarson et al. |
| 7,371,262 B2 | 5/2008 | Lecomte et al. |
| 7,377,944 B2 | 5/2008 | Janusson et al. |
| RE40,363 E | 6/2008 | Grim et al. |
| 7,381,860 B2 | 6/2008 | Gudnason et al. |
| 7,393,364 B2 | 7/2008 | Martin |
| 7,396,975 B2 | 7/2008 | Sigurjonsson et al. |
| 7,402,721 B2 | 7/2008 | Sigurjonsson et al. |
| 7,411,109 B2 | 8/2008 | Sigurjonsson et al. |
| D576,781 S | 9/2008 | Chang et al. |
| D577,828 S | 9/2008 | Ingimundarson et al. |
| 7,423,193 B2 | 9/2008 | Sigurjonsson et al. |
| 7,427,297 B2 | 9/2008 | Patterson et al. |
| 7,429,253 B2 | 9/2008 | Shimada et al. |
| 7,431,708 B2 | 10/2008 | Sreeramagiri |
| 7,431,737 B2 | 10/2008 | Ragnarsdottir et al. |
| 7,438,843 B2 | 10/2008 | Asgeirsson |
| 7,449,005 B2 | 11/2008 | Pickering et al. |
| 7,455,696 B2 | 11/2008 | Bisbee, III et al. |
| D583,956 S | 12/2008 | Chang et al. |
| 7,459,598 B2 | 12/2008 | Sigurjonsson et al. |
| 7,465,281 B2 | 12/2008 | Grim et al. |
| 7,465,283 B2 | 12/2008 | Grim et al. |
| 7,468,471 B2 | 12/2008 | Sigurjonsson et al. |
| 7,470,830 B2 | 12/2008 | Sigurjonsson et al. |

| Patent Number | Date | Inventor |
|---|---|---|
| 7,488,349 B2 | 2/2009 | Einarsson |
| 7,488,864 B2 | 2/2009 | Sigurjonsson et al. |
| D588,753 S | 3/2009 | Ingimundarson et al. |
| 7,503,937 B2 | 3/2009 | Asgeirsson et al. |
| 7,513,880 B2 | 4/2009 | Ingimundarson et al. |
| 7,513,881 B1 | 4/2009 | Grim et al. |
| D592,755 S | 5/2009 | Chang et al. |
| D592,756 S | 5/2009 | Chang et al. |
| 7,531,006 B2 | 5/2009 | Clausen et al. |
| 7,531,711 B2 | 5/2009 | Sigurjonsson et al. |
| 7,534,220 B2 | 5/2009 | Cormier et al. |
| 7,544,214 B2 | 6/2009 | Gramnas |
| 7,549,970 B2 | 6/2009 | Tweardy |
| D596,301 S | 7/2009 | Campos et al. |
| 7,578,799 B2 | 8/2009 | Thorsteinsson et al. |
| 7,581,454 B2 | 9/2009 | Clausen et al. |
| 7,597,672 B2 | 10/2009 | Kruijsen et al. |
| 7,597,674 B2 | 10/2009 | Hu et al. |
| 7,597,675 B2 | 10/2009 | Ingimundarson et al. |
| 7,618,463 B2 | 11/2009 | Oddsson et al. |
| 7,632,315 B2 | 12/2009 | Egilsson |
| 7,637,957 B2 | 12/2009 | Ragnarsdottir et al. |
| 7,637,959 B2 | 12/2009 | Clausen et al. |
| 7,641,700 B2 | 1/2010 | Yasui |
| 7,650,204 B2 | 1/2010 | Dariush |
| 7,662,191 B2 | 2/2010 | Asgeirsson |
| D611,322 S | 3/2010 | Robertson |
| 7,674,212 B2 | 3/2010 | Kruijsen et al. |
| 7,691,154 B2 | 4/2010 | Asgeirsson et al. |
| 7,696,400 B2 | 4/2010 | Sigurjonsson et al. |
| 7,704,218 B2 | 4/2010 | Einarsson et al. |
| D616,555 S | 5/2010 | Thorgilsdottir et al. |
| D616,556 S | 5/2010 | Hu |
| 7,713,225 B2 | 5/2010 | Ingimundarson et al. |
| D616,996 S | 6/2010 | Thorgilsdottir et al. |
| D616,997 S | 6/2010 | Thorgilsdottir et al. |
| D618,359 S | 6/2010 | Einarsson |
| 7,727,174 B2 | 6/2010 | Chang et al. |
| 7,736,394 B2 | 6/2010 | Bedard et al. |
| 7,745,682 B2 | 6/2010 | Sigurjonsson et al. |
| D620,124 S | 7/2010 | Einarsson |
| 7,749,183 B2 | 7/2010 | Ingimundarson et al. |
| 7,749,281 B2 | 7/2010 | Egilsson |
| 7,762,973 B2 | 7/2010 | Einarsson et al. |
| 7,771,488 B2 | 8/2010 | Asgeirsson et al. |
| 7,780,741 B2 | 8/2010 | Janusson et al. |
| 7,794,418 B2 | 9/2010 | Ingimundarson et al. |
| 7,794,505 B2 | 9/2010 | Clausen et al. |
| 7,811,333 B2 | 10/2010 | Jonsson et al. |
| 7,811,334 B2 | 10/2010 | Ragnarsdottir et al. |
| D627,079 S | 11/2010 | Robertson |
| 7,833,181 B2 | 11/2010 | Cormier et al. |
| 7,842,848 B2 | 11/2010 | Janusson et al. |
| D628,696 S | 12/2010 | Robertson |
| D629,115 S | 12/2010 | Robertson |
| 7,846,213 B2 | 12/2010 | Lecomte et al. |
| 7,862,620 B2 | 1/2011 | Clausen et al. |
| 7,863,797 B2 | 1/2011 | Calley |
| 7,867,182 B2 | 1/2011 | Iglesias et al. |
| 7,867,284 B2 | 1/2011 | Bedard |
| 7,867,285 B2 | 1/2011 | Clausen et al. |
| 7,867,286 B2 | 1/2011 | Einarsson |
| 7,868,511 B2 | 1/2011 | Calley |
| 7,879,110 B2 | 2/2011 | Phillips |
| 7,891,258 B2 | 2/2011 | Clausen et al. |
| 7,892,195 B2 | 2/2011 | Grim et al. |
| D634,438 S | 3/2011 | Hu |
| D634,852 S | 3/2011 | Hu |
| 7,896,826 B2 | 3/2011 | Hu et al. |
| 7,896,827 B2 | 3/2011 | Ingimundarson et al. |
| 7,896,927 B2 | 3/2011 | Clausen et al. |
| 7,909,884 B2 | 3/2011 | Egilsson et al. |
| 7,910,793 B2 | 3/2011 | Sigurjonsson et al. |
| 7,914,475 B2 | 3/2011 | Wyatt et al. |
| 7,918,765 B2 | 4/2011 | Kruijsen et al. |
| D637,942 S | 5/2011 | Lee et al. |
| 7,935,068 B2 | 5/2011 | Einarsson |
| D640,380 S | 6/2011 | Tweardy et al. |
| D640,381 S | 6/2011 | Tweardy et al. |
| 7,959,589 B2 | 6/2011 | Sreeramagiri et al. |
| D641,482 S | 7/2011 | Robertson et al. |
| D641,483 S | 7/2011 | Robertson et al. |
| 7,981,068 B2 | 7/2011 | Thorgilsdottir et al. |
| 7,985,193 B2 | 7/2011 | Thorsteinsson et al. |
| D643,537 S | 8/2011 | Lee |
| 7,998,221 B2 | 8/2011 | Lecomte et al. |
| 8,002,724 B2 | 8/2011 | Hu et al. |
| 8,007,544 B2 | 8/2011 | Jonsson et al. |
| 8,016,781 B2 | 9/2011 | Ingimundarson et al. |
| 8,021,317 B2 | 9/2011 | Arnold et al. |
| 8,025,632 B2 | 9/2011 | Einarsson |
| 8,025,699 B2 | 9/2011 | Lecomte et al. |
| 8,026,406 B2 | 9/2011 | Janusson et al. |
| D646,394 S | 10/2011 | Tweardy et al. |
| D647,622 S | 10/2011 | Lee et al. |
| D647,623 S | 10/2011 | Thorgilsdottir et al. |
| D647,624 S | 10/2011 | Thorgilsdottir et al. |
| 8,034,120 B2 | 10/2011 | Egilsson et al. |
| 8,038,636 B2 | 10/2011 | Thorgilsdottir et al. |
| 8,043,244 B2 | 10/2011 | Einarsson et al. |
| 8,043,245 B2 | 10/2011 | Campos et al. |
| 8,048,007 B2 | 11/2011 | Roy |
| 8,048,013 B2 | 11/2011 | Ingimundarson et al. |
| 8,048,172 B2 | 11/2011 | Jonsson et al. |
| 8,052,760 B2 | 11/2011 | Egilsson et al. |
| 8,057,550 B2 | 11/2011 | Clausen et al. |
| 2001/0029400 A1 | 10/2001 | Deffenbaugh et al. |
| 2002/0052663 A1 | 5/2002 | Herr et al. |
| 2002/0092724 A1 | 7/2002 | Koleda |
| 2002/0138153 A1 | 9/2002 | Koniuk |
| 2003/0093021 A1 | 5/2003 | Goffer |
| 2003/0125814 A1 | 7/2003 | Paasivaara et al. |
| 2003/0139783 A1 | 7/2003 | Kilgore et al. |
| 2003/0163206 A1 | 8/2003 | Yasui et al. |
| 2003/0195439 A1 | 10/2003 | Caselnova |
| 2004/0039454 A1 | 2/2004 | Herr et al. |
| 2004/0049290 A1 | 3/2004 | Bedard |
| 2004/0054423 A1 | 3/2004 | Martin |
| 2004/0064195 A1 | 4/2004 | Herr |
| 2004/0088025 A1 | 5/2004 | Gesotti |
| 2004/0181118 A1 | 9/2004 | Kochamba |
| 2004/0255711 A1* | 12/2004 | Takenaka et al. .......... 74/490.01 |
| 2004/0261561 A1* | 12/2004 | Takenaka et al. .......... 74/490.01 |
| 2005/0007834 A1 | 1/2005 | Hidaka |
| 2005/0049652 A1 | 3/2005 | Tong |
| 2005/0059908 A1 | 3/2005 | Bogert |
| 2005/0085948 A1 | 4/2005 | Herr et al. |
| 2005/0155444 A1 | 7/2005 | Otaki et al. |
| 2006/0004307 A1 | 1/2006 | Horst |
| 2006/0055358 A1* | 3/2006 | Ogawa et al. ............. 318/568.24 |
| 2006/0069448 A1 | 3/2006 | Yasui |
| 2006/0094989 A1 | 5/2006 | Scott et al. |
| 2006/0135883 A1 | 6/2006 | Jonsson |
| 2006/0214621 A1* | 9/2006 | Ogawa et al. ............. 318/568.12 |
| 2006/0224246 A1 | 10/2006 | Clausen et al. |
| 2006/0249315 A1 | 11/2006 | Herr et al. |
| 2006/0258967 A1 | 11/2006 | Fujil et al. |
| 2006/0276728 A1 | 12/2006 | Ashihara et al. |
| 2007/0016329 A1 | 1/2007 | Herr et al. |
| 2007/0043449 A1 | 2/2007 | Herr et al. |
| 2007/0123997 A1 | 5/2007 | Herr et al. |
| 2007/0162152 A1 | 7/2007 | Herr et al. |
| 2008/0114272 A1 | 5/2008 | Herr et al. |
| 2008/0155444 A1 | 6/2008 | Pannese et al. |
| 2009/0030530 A1 | 1/2009 | Martin |
| 2009/0222105 A1 | 9/2009 | Clausen |
| 2011/0224804 A1 | 9/2011 | Clausen et al. |
| 2011/0245931 A1 | 10/2011 | Clausen et al. |

FOREIGN PATENT DOCUMENTS

| | | |
|---|---|---|
| WO | WO-03068453 A1 | 8/2003 |
| WO | WO-2004017872 A1 | 3/2004 |
| WO | WO-2004019832 A1 | 3/2004 |
| WO | WO-2010027968 A2 | 3/2010 |

OTHER PUBLICATIONS

Blaya, J.A., and Herr, H., "Adaptive Control of a Variable-Impedance Ankle-Foot Orthosis to Assist Drop Foot Gait," Artificial Intelligence Lab and Harvard-MIT Division Health Sciences and Technology, Boston, MA, 30 pages.

Blaya, J.A., et al., "Active Ankle Foot Orthoses (AAFO)," http://www.ai,mit.edu. Artificial Intelligence Laboratory, Massachusetts Institute of Technology, Cambridge, Massachusetts, 3 pages.

Dollar, et al., "Lower Extremity Exoskeletions and Active Orthoses: Challenges and State-of-the-Art," IEEE Transcations on Robotics, vol. 24, No. 1, Feb. 2008, 15 pages.

Drake, C., "Foot & Ankle Splints or Orthoses," HemiHelp Information Sheet, London, United Kingdom, 3 pages, www.hemihelp.org.uk/leaflets/hbleaflets90.htm.

Hogan, N., "Impedance Control: An Approach to Manipulation," Dept. of Mechanical Engineering and Labortory of Manufacturing and Productivity, Massachusetts Institute of Technology, Cambridge MA, pp. 304-313, (Jun. 1984).

Hogan, N., "Impedance Control: An Approach to Manipulation: Part II—Implementation," Journal of Dynamic Systems, Measurement, and Control, 107:8-16, (1985).

Hogan, N., Impedance Control: An Approach to Manipulation: Part III—Application, Journal of Dynamics Systems, Measurement, and Control, 107:17-24, (1985).

Kim, et al., "Realization of Dynamic Walking for the Humaniod Robot Platform KHR-1," Advanced Robotics, vol. 18, No. 7, pp. 749-768, (2004).

Klute et al., "Powering Lower Limb Prosthestics with Muscle-Like Actuators," Abstract in: Proceeding of the 1st Annual Meeting of the VA Rehabilitation Research and Development Service, "Enabling Veterans: Meeting the Challenge of Rehabilitation in the Next Millennium," Washington, D.C., Oct. 1-3, 1998, p. 52.

Klute, et al., "Artificial Muscles: Actuators for Biorobotic Systems," The International Journal of Robotics Research, vol. 21, No. 4, Apr. 2002, pp. 295-309.

Klute, et al., Artificial Muscles: Actuators for Lower Limb Prostheses, Abstract in: Proceedings of the 2nd Annual Meeting of the VA rehabilitation Research and Development Service, Feb. 20-22, 2000, p. 107.

Klute, et al., "Artificial Tendons: Biomechanical Design Properties for Prosthetic Lower Limbs," Chicago 2000 World Congress on Medical Physics and Biomedical Engineering, Chicago on Jul. 24-28, 2000, 4 pages.

Klute, et al., Intelligent Transtibial Prostheses with Muscle-Like Actuators,: 2002 American Physiological Society Intersociety Meeting: The Power of Comparative Physiology: Evolution, Integration, and Applied, 1 page.

Klute, et al., "Lower Limb Prostheses Powered by Muscle-Like Pneumatic Actuator," Submitted to Oleodinamica e Pneumatica, Publishe Tecniche Nuove, Milamo, Italy, Mar. 15, 2000, 6 pages.

Klute, et al., "McKibben Artificial Muscles: Pneumatic Actuators with Biomechanical Intelligence," IEEE/ASME 1999 Inernational Conference on Advanced Intelligent Mechatronics, Atlanta, GA, Sep. 19-22, 1999, pp. 221-226.

Klute, et al., "Muscle-Like Pneumatic Actuators for Below-Knee Prostheses," Actuator2000:7th International Conference on New Actuators, Bremen, Germany on Jun. 9-21, 2000, pp. 289-292.

Klute, et al., "Variable Stiffness Prosthesis for Transtibial Amputees," Dept of Veteran Affairs, Seattle, WA USA, 2 pages.

International Search Report and Written Opinion for PCT/US2009/055600 mailed Apr. 29, 2010 (23 pages).

International Search Report and Written Opinion for PCT/US2010/047279 mailed Jan. 19, 2011 (11 pages).

International Search Report and Written Opinion for PCT/US2011/031105 mailed Oct. 11, 2011 (16 pages).

Abbas J. And Chizeck H., "Neural Network Control of Functional Neuromuscular Stimulation Systems: Computer Simulation Studies," IEEE Transactions on Biomedical Engineering, vol. 42, No. 1, Nov. 1995, pp. 1117-1127.

Abul-haj, C. and Hogan, N., "Functional assessment of control systems for cybernetic elbow prostheses. Part I, Part II," IEEE Transactions on Biomedical Engineering, vol. 37, No. 11, Nov. 1990, Cambridge, MA, pp. 1025-1047.

Akazawa, K., et. al, "Biomimetic EMG prosthesis-hand," Proceedings of the 18th Annual International Conference of the IEEE Engineering in Medicine and Biology Society, vol. 2, Oct. 1996, Amsterdam, Netherlands, pp. 535-536.

Aminian, "Estimation of Speed and Incline of Walking Using Neural Network," IEEE Transactions on Biomedical Engineering, vol. 44, No. 3, Jun. 1995, pp. 743-746.

Anderson, F. and Pandy M., "Dynamic optimization of human walking," Journal of Biomechanical Engineering, vol. 123, Oct. 2001, pp. 381-390.

Andrews, et al., "Hybrid FES Orthosis incorporating closed loop control and sensory feedback," J. Biomed Eng., vol. 10, Apr. 1988, pp. 189-195.

Arakawa, T. and Fukuda, T., "Natural motion generation of biped locomotion robot using hierarchical trajectory generation method consisting of GA, EP layers," Proceedings of the 1997 IEEE International Conference on Robotics and Automation, Apr. 1997, Albuquerque, NM, pp. 211-216.

Au., et. al., "Powered Ankle-Foot Prosthesis for the Improvement of Amputee Ambulation," Proceedings of the 29th Annual International Conference of the IEEE, Aug. 2007, Lyon, France, pp. 3020-3026.

Au, S. and Herr H., "Initial experimental study on dynamic interaction between an amputee and a powered ankle-foot prosthesis," Workshop on Dynamic Walking: Mechanics and Control of Human and Robot Locomotion, May 2006, Ann Arbor, MI, p. 1.

Au, S., et al. "An ankle-foot emulation system for the study of human walking biomechanics," Proc. of the 2006 IEEE Int. Conf. on Robotics and Automation, May 2006, Orlando, FL, pp. 2939-2945.

Au, S., et. al., "Biomechanical design of a powered ankle-foot prosthesis," Proc. of the 2007 IEEE Int. Conf. on Rehabilitation Robotics, Jun. 2007, Noordwijk, Netherlands, pp. 298-303.

Au, S., et. al., "Powered ankle-foot prosthesis to assist level-ground and stair-descent gaits," Neural Networks, vol. 21, No. 4, Mar. 2008, pp. 654-666.

Au, S., "An EMG-position controlled system for an active ankle-foot prosthesis: an initial experimental study," Proc. of the 2006 IEEE International Conference on Rehabilitation Robotics, Jul. 2005, Chicago, IL, pp. 375-379.

Au, S., et. al., "Powered Ankle-foot Prosthesis Improves Walking Metabolic Economy," IEEE Trans. on Robotics, vol. 25, No. 1, Feb. 2009, pp. 51-66.

Barth, D.., et. al., "Gait analysis and energy cost of below-knee amputees wearing six different prosthetic feet," Journal of Prosthetics & Orthotics, vol. 4, No. 2, Winter, 1992, pp. 63-75.

Baten, et al., "Inertial Sensing in Ambulatory back load Estimation," 18 Annual International Conferences of IEEE Engineering in Medicine and Biology Society, Amsterdam 1996, pp. 497-498.

Bateni, H. and Olney S., "Kinematic and kinetic variations of below-knee amputee gait," Journal of Prosthetics & Orthotics, vol. 14, No. 1, Mar. 2002, pp. 2-13.

Blaya, J. and Herr, H, "Adaptive control of a variable-impedance ankle-foot orthosis to assist drop-foot gait," IEEE Transactions on Neural Systems and Rehabilitation Engineering, vol. 12, No. 1, Mar. 2004, pp. 24-31.

Blickhan, R., "The spring-mass model for running and hopping," J of Biomech. 22, Feb. 1989, Great Britain, pp. 1217-1227.

Bortz, "A New Mathematical Formulation for Strapdown Inertial Navigation," IEEE Transactions of Aerospace and Electronic Systems, vol. AES-7, No. 1, Jan. 1971, p. 61-66.

Brockway, J., "Derivation of formulae used to calculate energy expenditure in man," Human Nutrition Clinical Nutrition, vol. 41, Nov. 1987, pp. 463-471.

Brown, R., "On the nature of the fundamental activity of the nervous centres: together with an analysis of the conditioning of rhythmic activity in progression, and a theory of the evolution of function in the nervous system," J Physiol, vol. 48, No. 1, Mar. 1914, pp. 18-46.

Chang, et al., Ischemic Colitis and Complications of Constipation Associated with the use of Alosetron Under a Risk Management Plan: Clinical Characteristics, Outcomes, and Incidences The Americal Journal of Gastronenterology, vol. 105, No. 4, Apr. 2010, pp. 866-875.

Chu, A., Kazerooni, H. and Zoss, A., "On the Biomimetic Design of the Berkeley Lower Extremity Exoskeleton (BLEEX)," Proceedings of the 2005 IEEE International Conference on Robotics and Automation, Apr. 2005, Barcelona, Spain, pp. 4356-4363.

Colborne, G. R., S. Naumann, P. E. Longmuir, and D. Berbrayer, "Analysis of mechanical and metabolic factors in the gait of congenital below knee amputees," Am. J. Phys. Med. Rehabil., vol. 92, pp. 272-278, Oct. 1992.

Collins, et al., "Supporting Online Material for Efficient bipedal robots based on passive-dynamic walkers," Mechanical Engineering, University of Michigan, Feb. 2005, Ann Arbor, MI, pp. 1-8.

Collins, et al., "Controlled Energy Storage and Return Prosthesis Reduces Metabolic cost of Walking," ASB 29th Annual Meeting, Cleveland, Ohio, Jul. 31-Aug. 5, 2005, 1 page.

Crago P., et. al., "New Control Strategies for neuroprosthetic systems," Journal of Rehabilitation Research and Development, vol. 33, No. 2, Apr. 1996, pp. 158-172.

Daley, M. A., Felix, G., Biewener, A. A., 2007. Running stability is enhanced by a proximo-distal gradient in joint neuromechanical control. J Exp Biol 210 (Pt 3), Nov. 2006, pp. 383-394.

Dapena, J. and McDonald, C., "Three-dimensional analysis of angular momentum in the hammer throw," Med. Sci. in Sports Exerc., vol. 21, No. 2, Apr. 1989, pp. 206-220.

Dietz, V., "Proprioception and locomotor disorders," Nat Rev Neurosci, vol. 3, Oct. 2002, pp. 781-790.

Dietz, V., "Spinal Cord Pattern Generators for Locomotion," download Feb. 6, 2012, http://www.Clinph-journal.com/article/PIIS1388245703001202/fulltext, 12 pages.

Doerschuk, et. al., "Upper extremity limb function discrimination using EMG signal analysis," IEEE Transactions on Biomedical Engineering. vol. 30., No. 1., Jan. 1983, pp. 18-28.

Doke, J., et. al., "Mechanics and energetics of swinging the human leg," The Journal of Experimental Biology, vol. 208, Feb. 2005, pp. 439-445.

Donelan, J., et. al., "Force regulation of ankle extensor muscle activity in freely walking cats," J Neurophysiol, vol. 101, No. 1, Nov. 2008, pp. 360-371.

Donelan, J., et. al., "Mechanical work for step-to-step transitions is a major determinant of the metabolic cost of human walking," J. Exp. Biol., vol. 205, Dec. 2002, pp. 3717-3727.

Donelan, J., et. al. "Simultaneous positive and negative external mechanical work in human walking," Journal of Biomechanics, vol. 35, Jan. 2002, pp. 117-124.

Drake, C., "Ankle & Foot Splints or Orthoses," HemiHelp, Information Sheet 13 Last updated Jun. 2009, 5 pages.

Drake, C., "Ankle & Foot Splints or Orthoses (AFOs)," HemiHelp, Last updated Jun. 2009, 8 pages.

Drake, C., "Foot & Ankle Splints or Orthoses," HemiHelp Information Sheet, London, United Kingdom, www.hemihelp.org.uk/leaflets/hbleaflets90.htm, pp. 1-3.

Eilenberg, M., "A Neuromuscular-Model Based Control Strategy for Powered Ankle-Foot Prostheses," Masters Thesis, Massachusetts Institute of Technology, Cambridge, Mass., 2009.

Ekeberg, O. and Grillner, S., "Simulations of neuromuscular control in lamprey swimming," Philos Trans R Soc Lond B Biol Sci, vol. 354, May 1999, pp. 895-902.

Ekeberg, O. and Pearson, K., "Computer simulation of stepping in the hind legs of the cat: an examination of mechanisms regulating the stance-to-swing transition," J Neurophysiol, vol. 94, No. 6, Jul. 2005, pp. 4256-4268.

Endo, K., et. al., "A quasi-passive model of human leg function in level-ground walking," Proc. of 2006 IEEE/RSJ International Conference on Intelligent Robots and Systems (IROS), Oct. 2006, Beijing, China, pp. 4935-4939.

Eppinger, S. Seering W., "Three dynamic problems in robot force control," IEEE Transactions on Robotics and Automation, vol. 8, No. 6, Dec. 1992, pp. 751-758.

Esquenazi, A. and DiGiacomo, R., "Rehabilitation After Amputation," Journ Am Podiatr Med Assoc, vol. 91, No. 1, Jan. 2001, pp. 13-22.

Farley, C. and McMahon, T., "Energetics of walking and running: insights from simulated reduced-gravity experiments," The American Physiological Society, Dec. 1992, pp. 2709-2712.

Farry, K. A., et al., "Myoelectric teleoperation of a complex robotic hand," IEEE Transactions on Robotics and Automation. vol. 12, No. 5, Oct. 1996, pp. 775-788.

Featherstone, R., 1987, "Robot Dynamic Algorithms", Boston, Mass., Kluwer Academic Publishers, pp. 155-172.

Fite, K., et. al., "Design and Control of an Electrically Powered Knee Prosthesis," Proc. of 2007 IEEE 10th International Conference on Rehabilitation Robotics (ICORR), Jun. 2007, pp. 902-905.

Flowers, W. "A Man-Interactive Simulator System for Above-Knee Prosthetic Studies," Ph.D. thesis, Massachusetts of Institute Technology, Department of Mechanical Engineering. Jul. 10, 1973.

Fod, A., et. al., "Automated Derivation of Primitives for Movements Classification," Autonomous Robots, vol. 12, No. 1, Jan. 2002, pp. 39-54.

Frigon, A. and Rossignol, S., "Experiments and models of sensorimotor interactions during locomotion," Biol Cybern, vol. 95, No. 6, Nov. 2006, pp. 607-627.

Fujita K, et. al., "Joint angle control with command filter for human ankle movement using functional electrical stimulation," Proc. of IEEE Ninth Annual Conference for the Engineering in Medicine and Biology Society, Nov. 1987, Boston, MA, pp. 1719-1720.

Fukuda, O. et al., "A human-assisting manipulator teleoperated by EMG signals and arm motions," IEEE Transactions on Robotics and Automation. vol. 19, No. 2, Apr. 2003, pp. 210-222.

Gates, D., "Characterizing ankle function during stair ascent, descent, and level walking for ankle prosthesis and orthosis design," Masters thesis, Boston University, 2004, pp. 1-82.

Geiritsen, K., et. al., "Direct dynamics simulation of the impact phase in heel-toe running," J. Biomech., vol. 28, No. 6, Jun. 1995, Great Britain, pp. 661-668.

Geyer, H., et. al., "Positive force feedback in bouncing gaits?," Proceedings of Royal Society B-Biological Sciences, vol. 270, No. 1529, Aug. 2003, pp. 2173-2183, 2003.

Geyer, H. and Herr H., "A muscle-reflex model that encodes principles of legged mechanics predicts human walking dynamics and muscle activities," IEEE Transactions on Neural Systems and Rehabilitations Engineering, vol. 18, No. 3, Jun. 2010, pp. 263-273.

Geyer, H., et. al., "Compliant leg behaviour explains the basic dynamics of walking and running," Proc. R. Soc. Cond. B 273, Aug. 2006, pp. 2861-2867.

Ghigliazza, R., et. al., "A simply stabilized running model," SIAM J. Applied. Dynamical Systems, vol. 2, No. 2, May 2004, pp. 187-218.

Godha, el al., "Integrated GPS/INS System for Pedestrian Navigation in a Signal Degraded Environment," ION GNSS, Sep. 2006, Fort Worth, TX, pp. 1-14.

Goswami, A., "Postural stability of biped robots and the foot-rotation indicator (FRI) point," International Journal of Robotics Research, vol. 18, No. 6, Jun. 1999, pp. 523-533.

Goswami, A. and Kallem, V., "Rate of change of angular momentum and balance maintenance of biped robots," Proceedings of the 2004 IEEE International Conference on Robotics and Automation, Apr. 2004, New Orleans, La., pp. 3785-3790.

Graupe, D., et al., "A microprocessor system for multifunctional control of upper-limb prostheses via myoelectric signal identification," IEEE Transaction on Automatic Control. vol. AC-23, vol. 4, Aug. 1978, pp. 538-544.

Gregoire, L., and et al, "Role of mono- and bi-articular muscles in explosive movements," International Journal of Sports Medicine 5, 614-630. Dec. 1984.

Grillner, S. and Zangger, P., "On the central generation of locomotion in the low spinal cat," Exp Brain Res, vol. 34, No. 2, Jan. 1979, pp. 241-261.

Grimes, D. L., "An active multi-mode above-knee prosthesis controller," Ph.D. Thesis, Massachusetts Institute of Technology, Jul. 20, 1979.

Gu, W., "The Regulation of Angular Momentum During Human Walking," Undergraduate Thesis, Massachusetts Institute of Technology, Physics Department, Jun. 2003, pp. 2-48.

Gunther, M., et. al., "Human leg design: optimal axial alignment under constraints," J. Math. Biol., vol. 48, Mar. 2004, pp. 623-646.

Gunther, M. and Ruder, H., "Synthesis of two-dimensional human walking: a test of the A-model," Biol. Cybern., vol. 89, May 2003, pp. 89-106.

Hanafusa et al., "A Robot Hand with Elastic Fingers and Its Application to Assembly Process," pp. 337-359, Robot Motion, Brady et al., MIT Press, Cambridge, MA, 1982.

Hansen, A. H., Childress, D. S., Miff, S. C., Gard, S. A., Mesplay, K. P., "The human ankle during walking: implication for the design of biomimetic ankle prosthesis," Journal of Biomechanics, vol. 37, No. 10, Oct. 2004, pp. 1467-1474.

Hayes et al., "Leg Motion Analysis During Gait by Multiaxial Accelerometry: Theoretical Foundations and Preliminary Validations," Journal of Biomechanical Engineering, vol. 105, Aug. 1983, pp. 283-289.

Heglund, N., "A Simple Design for a Force-Plat to Measure Ground Reaction Forces," J. Exp. Biol., vol. 93, Aug. 1981, pp. 333-338.

Herr, H., et. al, "A model of scale effects in mammalian quadrupedal running," J Exp Biol 205 (Pt 7), Apr. 2002, pp. 959-967.

Herr, H. and Wilkenfeld A., "User-adaptive control of a magnetorheologicalprosthetic knee," Industrial Robot: An International Journal, vol. 30, No. 1, 2003, pp. 42-55.

Herr, H. and Popovic, M., "Angular momentum regulation in human walking," J. Exp. Biol., vol. 211, Feb. 2008, pp. 467-481.

Herr, H. and McMahon, T.,"A trotting horse model," Int. J. Robotics Res., vol. 19, No. 6, Jun. 2000, pp. 566-581.

Heyn et al., "The Kinematice of the Swing Phase Obtained from Accelerometer and Gyroscope Measurements," 18$^{th}$ Annual International Conference of the IEEE Engineering in Medicine and Biology Society, Nov. 1996, Amsterdam, Netherlands, pp. 463-464.

Hill, V., "The heat of shortening and the dynamic constants of muscle," Proceedings of the Royal Society London B, vol. 126, No. 843, Oct. 1938, pp. 136-195.

Hirai, K., et al., "The development of Honda humanoid robot," Proceedings on IEEE/RSJ International Conference on Intelligent Robots and Systems, May 1998, Leuven, Belgium, pp. 1321-1326.

Hitt, J., R. Bellman, M. Holgate, T. Sugar, and K. Hollander, "The sparky (spring ankle with regenerative kinetics) projects: Design and analysis of a robotic transtibial prosthesis with regenerative kinetics," in Proc. IEEE Int. Conf. Robot. Autom. Orlando, Fla., pp. 2939-2945, Sep. 2007.

Hof. A., et. al., "Calf muscle moment, work and efficiency in level walking; role of series elasticity," Journal of Biomechanics, vol. 16, No. 7, Sep. 1983, pp. 523-537.

Hofbaur, M. and Williams, B., "Hybrid Diagnosis with Unknown Behavioral Modes", Proceedings of the 13.sup.th International Workshop on Principles of Diagnosis (DX02), May 2002, pp. 1-10.

Hofbaur, M. and Williams, B., "Mode Estimation of Probabilistic Hybrid Systems", HSSC 2002, LNCS 2289, Mar. 25, 2002, pp. 253-266.

Hofmann, A., et. al., "A Sliding Controller for Bipedal Balancing Using Integrated Movement of Contact and Non-Contact Limbs," Proceedings of the IEEE/RSJ International Conference on Intelligent Robots and Systems, Sep. 2004, Sendai, Japan, pp. 1952-1959.

Hofmann, A., et. al., "Robust Execution of Bipedal Walking Tasks from Biomechanical Principles," Doctor of Philosophy at the Massachusetts Institute of Technology, Jan. 2006, 407 pages.

Hogan, N and Buerger S., "Impedance and Interaction Control," Robotics and Automation Handbook, CRC Press, Jun. 2004, pp. 19.1-19.24.

Hogan, N. (1976) A review of the methods of processing EMG for use as a proportional control signal. Biomedical Engineering. pp. 81-86.

Hogan, N., "Impedance Control: An Approach to Manipulation: Part I—Theory," Journal of Dynamic Systems, Measurement , and Control, vol. 107, Mar. 1985, pp. 1-7.

Hollander, K. W., T. G. Sugar, and D. E. Herring, "Adjustable robotic tendon using a 'Jack Springs'.TM.," Proceedings on IEEE International Conference on Rehabilitation Robotics, Chicago, pp. 113-118, Jun. 28, 2005.

Howard, "Joint and Actuator Design for Enhanced Stability in Robotic Force Control," Ph.D. thesis, Massachusetts Inst. of Technology, Dept. of Aeronautics and Astronautics, Sep. 19, 1990.

Huang, H. and Chen. C., "Development of a myoelectric discrimination system for a multi-degree prosthetic hand," Proceeding of the 1999 IEEE International Conference on Robotics and Automation, May 1999, Detroit, MI, pp. 2392-2397.

Huang, Q., "Planning walking patterns for a biped robot," IEEE Transactions on Robotics and Automation, vol. 17, No. 3, Jun. 2001, pp. 280-289.

Hultborn, H., Spinal reflexes, mechanisms and concepts: from Eccles to Lundberg and beyond, Prog Neurobiol, vol. 78, Feb. 2006, pp. 215-232.

Ijspeert, A. J., 2008, "Central pattern generators for locomotion control in animals and robots: a review," Neural Netw, vol. 21, No. 4, May 2008, pp. 642-653.

Ijspeert, A., et. al., "From swimming to walking with a salamander robot driven by a spinal cord model," Science, vol. 315, No. 5817, Mar. 2007, pp. 1416-1420.

International Preliminary Search Report for PCT/US10/047279 mailed Mar. 15, 2012, IWK-002PC, 7 pages.

Ivashko, D., et. al, "Modeling the spinal cord neural circuitry controlling cat hindlimb movement during locomotion," Neurocomputing, vol. 52-54, Mar. 2003, pp. 621-629.

Johansson, J., et al., "A clinical comparison of variable damping and mechanically passive prosthetic knee devices," American Journal of Physical Medicine & Rehabilitation, vol. 84, No. 8, Aug. 2005, pp. 563-575.

Johnson, C. and Lorenz R., "Experimental identification of friction and its compensation in precise, position controlled mechanisms," IEEE Trans. on Industry Applications, vol. 28, No. 6, Dec. 1992, pp. 1392-1398.

Jonic S, et. al., "Three machine learning techniques for automatic determination of rules to control locomotion," IEEE Trans Biomed Eng, vol. 46, No. 3, Mar. 1999, pp. 300-310.

Kadaba, M., et. al., "Measurement of lower extremity kinematics during level walking," J. Orthop. Res., vol. 8, May 1990, pp. 383-392.

Kadaba, M., et. al., "Repeatability of kinematic, kinetic, and electromyographic data in normal adult gait," J. Orthop. Res., vol. 7, Nov. 1989, pp. 849-860.

Kajita, K., et. al., "Biped walking on a low friction floor," Proceedings of the 2004 IEEE/RSJ International Conference on Intelligent Robots and Systems, Oct. 2004, Sendai, Japan., pp. 3546-3551.

Kajita, S., et. al., "Resolved Momentum Control: Humanoid Motion Planning based on the Linear and Angular Momentum," Proceedings of the 2003 IEEE/RSJ International Conference on Intelligent Robots and Systems, Oct. 2003, Las Vegas, Nev., pp. 1644-1650.

Kajita, S., et. al., "A Hop towards Running Humanoid Biped," Proceedings of the 2004 IEEE International Conference on Robotics and Automation, Apr. 2004, New Orleans, La., pp. 629-635.

Kaneko, K., et al., "Humanoid robot HRP-2," Proc. IEEE Int. Conf. on Robotics and Automation, Apr. 2004, New Orleans, La., pp. 1083-1090.

Kapti, A. and Yucenur M., "Design and control of an active artificial knee joint," Mechanism and Machine Theory, vol. 41, Apr. 2006, pp. 1477-1485.

Katic, D. and Vukobratovic, M., "Survey of intelligent control techniques for humanoid robots," Journal of Intelligent and Robotics Systems, vol. 37, Jun. 2003, pp. 117-141.

Kerrigan, D, et. al., "A refined view of thedeterminants of gait: significance of heel rise," Arch. Phys. Med. Rehab., vol. 81, Aug. 2000, pp. 1077-1080.

Kerrigan, D, et. al., "Quantification of pelvic rotation as a determinant of gait," Arch. Phys. Med. Rehab., vol. 82, Feb. 2001, pp. 217-220.

Khatib, O., et. al., "Coordination and decentralized cooperation of multiple mobile manipulators," Journal of Robotic Systems, vol. 13, No. 11, Nov. 1996, pp. 755-764.

Khatib, O., et. al., "Whole body dynamic behavior and control of human-like robots," International Journal of Humanoid Robotics, vol. 1, No. 1, Mar. 2004, pp. 29-43.

Kidder, et al., "A System for the Analysis of Foot and Ankle Kinematics During Gait," IEEE Transactions on Rehabilitation Engineering, vol. 4, No. 1, Mar. 1996, pp. 25-32.

Kim, et al., "Realization of Dynamic Walking for the Humaniod Robot Platform KHR-1," Advanced Robotics, vol. 18, No. 7, 2004, pp. 749-768.

Kirkwood C, et. al., "Automatic detection of gait events: a case study using inductive learning techniques.," J Biomed Eng, vol. 11, Nov. 1989, pp. 511-516.

Kitayama, I., Nakagawa N, Amemori K, "A microcomputer controlled intelligent A/K prosthesis," Proceedings of the 7th' World Congress of the International Society for Prosthetics and Orthotics, Chicago. Jun. 28, 1992.

Klute, G., et. al., "Mechanical properties of prosthetic limbs adapting to the patient," Journal of Rehabilitation Research and Development, vol. 38, No. 3, May 2001, pp. 299-307.

Koganezawa, K. and Kato, I., "Control aspects of artificial leg," IFAC Control Aspects of Biomedical Engineering, 1987, pp. 71-85.

Kondak, K. and Hommel, G., "Control and online computation of stable movement for biped robots," Proc. of the 2003 IEEE/RSJ International Conference on Intelligent Robots and Systems (IROS), Oct. 2003, Las Vegas, Nev., pp. 874-879.

Kostov A., et. al., "Machine learning in control of functional electrical stimulation (FES) systems for locomotion," IEEE Trans on Biomed Eng, vol. 42, No. 6, Jun. 1995, pp. 541-551.

Kuo, A., "A simple model of bipedal walking predicts the preferred speed-step length relationship," Journal of Biomechanical Engineering, vol. 123, Jun. 2001, pp. 264-269.

Kuo, A., "Energetics of actively powered locomotion using the simplest walking model," Journal of Biomechanical Engineering, vol. 124, Feb. 2002, pp. 113-120.

LaFortune, "Three-Dimensional Acceleration of the Tibia During Walking and Running," J. Biomechanics, vol. 24, No. 10, 1991, pp. 877-886.

LeBlanc, M. and Dapena, J., "Generation and transfer of angular momentum in the javelin throw," Presented at the 20th annual meeting of the American Society of Biomechanics, Oct. 1996, Atlanta, Ga., pp. 17-19.

Liu, X., Low, K. H., Yu, H. Y., (2004) 'Development of a Lower Extremity Exoskeleton for Human performance Enhancement', IEEE Conf. on Intelligent Robots and Systems, Sendai, Japan.

Light, et. al., Skeletal Transients on Heel Strike in Normal Walking With Different Footwear. J. Biomechanics vol. 13, pp. 477-480.

Lloyd R. and Cooke C., "Kinetic changes associated with load carriage using two rucksack designs," Ergonomics, vol. 43, No. 9, Sep. 2000, pp. 1331-1341.

Luinge, "Inertial Sensing of Human Movement," Twente University Press, ISBN 9036518237, 2002, pp. 1-80.

Lundberg, A., Oct. 19, 1968. Reflex control of stepping. In: The Nansen memorial lecture V, Oslo: Universitetsforlaget, 5-42.

Macfarlane, P., "Gait comparisons for below-knee amputees using a flex-foot versus a conventional prosthetic foot," Journal of Prosthetics & Orthotics, vol. 3, No. 4, Summer, 1991, pp. 150-161.

Maganaris, C., "Force-length characteristics of in vivo human skeletal muscle," Acta Physiol. Scand., vol. 172, Aug. 2001, pp. 279-285.

Maganaris, C., "Force-length characteristics of the in vivo human gastrocnemius muscle," Clin. Anat., vol. 16, May 2003, pp. 215-223.

Martens, W.L.J., "Exploring the Information Content and Some Applications of Body Mounted Piezo-Resistive Accelerometers," in: P.H. Veltink and R.C. van Lummel (eds.), Dynamic Analysis using Body Fixed Sensors, ISBN 90-9007328-0, 1994, pp. 8-11.

Maufroy, C., Towards a general neural controller for quadrupedal locomotion, Neural Netw, vol. 21, No. 4, Apr. 2008, pp. 667-681.

Mayagoitia R., et al., "Accelerometer and rate gyroscope measurement of kinematics: an inexpensive alternative to optical motion analysis systems," Journal of Biomechanics, vol. 35, Apr. 2002, pp. 537-542.

McGeer T., "Passive Dynamic Walking," International Journal of Robotics, vol. 9, No. 2, May 1988, pp. 62-82.

McGeer, T., "Principles of walking and running," Advances in Comparative and Environmental Physiology, vol. 11, Ch. 4, Apr. 1992, pp. 113-139.

McIntosh, A., et. al., "Gait dynamics on an inclined walkway," Journal of Biomechanics, vol. 39, Sep. 2005, pp. 2491-2502.

McMahon, T., "The mechanics of running: how does stiffness couple with speed?," J. of Biomecb., vol. 23, 1990, pp. 65-78.

McMahon, T., et. al., "Groucho Running," Journal of Applied Physiology, vol. 62, No. 6, Jun. 1987, pp. 2326-2337.

Minassian, K., et. al., "Human lumbar cord circuitries can be activated by extrinsic tonic input to generate locomotor-like activity," Hum. Mov. Sci., vol. 26, Mar. 2007, pp. 275-295.

Mochon, S., et. al., "Ballistic walking," Journal of Biomechanics, vol. 13, Dec. 1980, pp. 49-57.

Molen, N., "Energy/speed relation of below-knee amputees walking on motor-driven treadmill," Int. Z. Angew. Physio, vol. 31, Mar. 1973, pp. 173.

Morris, "Accelerometry—A Technique for the Measurement of Human Body Movements," J. Biomechanics, vol. 6, Nov. 1973, pp. 729-736.

Muraoka, T., et. al, "Muscle fiber and tendon length changes in the human vastus lateralis during slow pedaling," J. Appl. Physiol., vol. 91, Nov. 2001, pp. 2035-2040.

Nakagawa A., "Intelligent Knee Mechanism and the Possibility to Apply the Principle to the Other Joints," Proceedings of the $20^{th}$ Annual International Conference of the IEEE Engineering in Medicine and Biology Society, Vo. 20, No. 5, Oct. 1998, pp. 2282-2287.

Neal R. and Hinton G., "A view of the EM algorithm that justifies incremental, sparse, and other variants," In Michael I. Jordan (editor), Learning in Graphical Models, 1999, Cambridge, MA, pp. 1-14.

Ng, et al., "Fuzzy Model Identification for Classification of Gait Events in Paraplegics," IEEE Transactions on Fuzzy Systems, vol. 5, No. 4, Nov. 1997, pp. 536-544.

Nielsen, D., et. al., "Comparison of energy cost and gait efficiency during ambulation in below-knee amputees using different prosthetic feet—a preliminary report," Journal of Prosthetics & Orthotics, vol. 1, No. 1, 1989, pp. 24-29.

Ogihara, N. and Yama7aki, N., "Generation of human bipedal locomotion by a bio-mimetic neuro-musculo-skeletal model," Biol Cybern, vol. 84, No. 1, Jan. 2001, pp. 1-11.

Palmer, M., "Sagittal plane characterization of normal human ankle function across a range of walking gait speeds," Master's Thesis, MIT, Feb. 2002, Cambridge, MA, pp. 1-71.

Paluska, D., and Herr, H., "The effect of series elasticity on actuator power and work output: implications for robotic and prosthetic joint design," Robotics and Autonomous Systems, vol. 54, Jun. 2006, pp. 667-673.

Paluska, D. and Herr, H., "Series Elasticity and Actuator Power Output," Proceedings of the 2006 IEEE International Conference on Robotics and Automation, May 2006, Orlando, FL, pp. 1830-1833.

Pang, M., et. al., "The initiation of the swing phase in human infant stepping: importance of hip position and leg loading," J Physiol, vol. 528, No. 2, Oct. 2000, pp. 389-404.

Pasch, K. A., and W. P. Seering, "On the drive systems for high performance machines," AMSE J. Mechanisms, Transmissions, and Automation in Design vol. 106, pp. 102-108, Mar. 1984.

Paul, C., et. al., "Development of a human neuro-musculo-skeletal model for investigation of spinal cord injury," Biol Cybern, vol. 93, No. 3, Aug. 2005, pp. 153-170.

Pearson, K., "Generating the walking gait: role of sensory feedback," Prog Brain Res, vol. 143, 2004, pp. 123-129.

Pearson, K., et. al., "Assessing sensory function in locomotor systems using neuro-mechanical simulations," Trends Neurosci, vol. 29, No. 11, Nov. 2006, pp. 625-631.

Perry, Gait Analysis: Normal and Pathological Function, New Jersey: SLACK Inc.; 1992, Book Review, 1 page.

Perry, J. and S. Shanfield, "Efficiency of dynamic elastic response prosthetic feet," Journal of Rehabilitation Research and Development, vol. 30, No. 1, 1993 pp. 137-143.

Petrofshy et al., "Feedback Control System for Walking in Man," Comput. Biol. Med., vol. 14, No. 2, Mar. 1984, pp. 135-149.

Pfeffer et al., "Experiments with a Dual-Armed, Cooperative, Flexible-Drivetrain Robot System," Proc. 1993 IEEE Int. Conf. on Robotics & Automation, vol. 3, pp. 601-608, May 5, 1993.

Popovic D., et al., "Control Aspects of Active Above-Knee Prosthesis," Int. Journal Man-Machine Studies, (1991) 35, pp. 751-767.

Popovic, D., "Control of Movement for the Physically Disabled," Springer-Verlag London Limited, May 2000, pp. 270-302.

Popovic, M. and Herr, H., "Global Motion Control and Support Base Planning," Proceedings of the IEEE/RSJ International Conference on Intelligent Robots and Systems, Aug. 2005, Alberta, Canada, pp. 1-8.

Popovic, M., et. al., "Angular Momentum Regulation during human walking: Biomechanics and Control," Proceedings of the 2004 IEEE International Conference on Robotics and Automation, Apr. 2004, New Orleans, LA, pp. 2405-2411.

Popovic, M., et. al., "Zero spin angular momentum control: definition and applicability," Proceedings of the IEEE-RAS/RSJ International Conference on Humanoid Robots, Nov. 2004, Los Angeles, CA, pp. 1-16.

Popovic, M., "Angular Momentum Primitives for Human Walking: Biomechanics and Control," Proc. of the 2004 IEEE/RSJ International Conference on Intelligent Robots and Systems, Sep. 2004, Sendai, Japan., pp. 1685-1691.

Popovic, et al., "Gait Identification and Recognition Sensor," Proceedings of 6th Vienna International Workshop on Functional Electrostimulation, Sep. 1998, pp. 1-4.

Popovic, M., et. al., "Ground Reference Points in Legged Locomotion: Definitions, Biological Trajectories and Control Implications," International Journal of Robotics Research, Dec. 2006, pp. 79-104.

Popovic, M.B., W. Gu and H. Herr, "Conservation of Angular Momentum in Human Movement," MIT AI Laboratory-Research Abstracts, Sep. 2002. pp. 231-232, 2002.

Pratt, G. and Williamson M., "Series elastic actuators," Proceedings on IEEE/RSJ International Conference on Intelligent Robots and Systems, Jan. 1995, Pittsburgh, PA, pp. 399-406.

Pratt, G., "Legged Robots: What's New Since Raibert," IEEE Robotics and Automation Magazine, Research Perspectives, Sep. 2000, pp. 15-19.

Pratt, G., "Low Impedance Walking Robots," Integ. and Comp. Biol., vol. 42, Feb. 2002, pp. 174-181.

Pratt, J., et. al., "The RoboKnee: An Exoskeleton for Enhancing Strength and Endurance During Walking", IEEE Conf. on Robotics and Automation, Apr. 2004, New Orleans, LA, pp. 2430-2435.

Prochazka, A., et. al., "Positive force feedback control of muscles," J. of Neuro-phys., vol. 77, Jun. 1997, pp. 3226-3236.

Prochazka, A., et. al., "Sensory control of locomotion: reflexes versus higher-level control," Adv Exp Med Biol, vol. 508, 2002, pp. 357-367.

Prochazka, A. and Yakovenko, S., "The neuromechanical tuning hypothesis," Prog Brain Res, vol. 165, Oct. 2007, pp. 255-265.

Raibert, M., "Legged Robots that Balance," The MIT Press, Nov. 1986, Cambridge, MA, p. 89.

Rassier, D., et. al., "Length dependence of active force production in skeletal muscle," Journal of Applied Physiology, vol. 86, Issue 5, May 1999, pp. 1455-1457.

Riener, R., et. al., "Stair ascent and descent at different inclinations," Gait Posture, vol. 15, Feb. 2002, pp. 32-44.

Reitman, et. al., Gait analysis in prosthetics: opinions, ideas and conclusions, Prosthetics and Orthotics International, 2002, 26, 50-57.

Robinson, D., "Series elastic actuator development for a biomimetic walking robot," Proceedings of IEEE/ASME International Conference on Advanced Intelligent Mechatronics, Sep. 1999, pp. 561-568.

Robinson, D., "Design and an analysis of series elasticity in closed-loop actuator force control," Ph.D. Thesis, MIT, Jun. 2000, Cambridge, MA, pp. 1-123.

Rosen, J., et al., "A myosignal-based powered exoskeleton system," IEEE Transactions on Systems, Man, and Cybernetics—Part A: Systems and Humans, vol. 31, No. 3, May 2001, pp. 210-222.

Ruina, A., et. al., "A collisional model of the energetic cost of support work qualitatively explains leg sequencing in walking and galloping, pseudo-elastic leg behavior in running and the walk-to-run transition," Journal of Theoretical Biology, vol. 237, Issue 2, Jun. 2005, pp. 170-192.

Rybak, I., et. al., "Modelling spinal circuitry involved in locomotor pattern generation: insights from deletions during fictive locomotion," J Physiol, vol. 577 (Pt 2), Dec. 2001, 617-639.

Sanderson, D., et. al., "Lower extremity kinematic and kinetic adaptations in unilateral below-knee amputees during walking," Gait and Posture, vol. 6, No. 2, Oct. 1997, pp. 126-136.

Sanger, T., "Human arm movements described by a low-dimensional superposition of principal component," Journal of NeuroScience, vol. 20, No. 3, Feb. 2000, pp. 1066-1072.

Saranli, U., "RHex: A simple and highly mobile hexapod robot," Int. Jour. Rob. Res., vol. 20, No. 7, Jul. 2001, pp. 616-631.

Sarrigeorgidis K. and Kyriakopoulos K., "Motion control of the N.T.U.A. robotic snamek on a planar surface," Proc. of the 1998 IEEE International Conference on Robotics and Automation, May 1998, pp. 2977-2982.

Schaal, S. and Atkeson, C., "Constructive incremental learning from only local information," Neural Computation, vol. 10, No. 8, Nov. 1998, pp. 2047-2084.

Schaal, S., "Is imitation learning the route to humanoid robots?" Trends in Cognitive Sciences, vol. 3, Jun. 1999, pp. 233-242.

Scott, S. and Winter, D., "Biomechanical model of the human foot: kinematics and kinetics during the stance phase of walking," J. Biomech., vol. 26, No. 9, Sep. 1993, 1091-1104.

Sentis, L. and O. Khatib, "Task-Oriented Control of Humanoid Robots Through Prioritization," IEEE-RAS/RSJ International Conference on Humanoid Robots, Nov. 2004, Santa Monica, CA, pp. 1-16.

Seyfarth, A., et. al., "A movement criterion for running," J. of Biomech., vol. 35, May 2002, pp. 649-655.

Seyfarth, A., "Swing-leg retraction: a simple control model for stable running," J. Exp. Biol., vol. 206, Aug. 2003, pp. 2547-2555.

Seyfarth, A., et. al., "Stable operation of an elastic three-segmented leg," Biol.Cybern., vol. 84, 2001, pp. 365-382.

Simon F., et. al, "Convergent force fields organized in the frog's spinal cord," Journal of NeuroScience, vol. 13, No. 2, Feb. 1993, pp. 467-491.

Sinkjaer, T., et. al., "Major role for sensory feedback in soleus EMG activity in the stance phase of walking in man," J Physiol, vol. 523, No. 3, Mar. 2000, 817-827.

Skinner, H. and Effeney D., "Gait analysis in amputees," Am J Phys Med, vol. 64, Apr. 1985, pp. 82-89.

Smidt et al., "An Automated Accelerometry System for Gait Analysis," J. Biomechanics, vol. 10, 1977, pp. 367-375.

Srinivasan, M., "Energetics of legged locomotion: Why is total metabolic cost proportional to the cost of stance work," Proc. on ISB XXth Congress and the American Society of Biomechanics Annual Meeting, Jul. 2003, Cleveland, OH, pp. 829.

Stepien, J., et al., "Activity Levels Among Lower-Limb Amputees: Self-Report Versus Step Activity Monitor," Arch. Phys. Med. Rehabil., vol. 88, No. 7, Jul. 2007, pp. 896-900.

Sugano et al., "Force Control of the Robot Finger Joint equipped with Mechanical Compliance Adjuster," Proc. of the 1992 IEEE/RSJ Int. Conf. on Intell. Robots & Sys., Jul. 1992, pp. 2005-2013.

Sugihara, T., et. al., "Realtime Humanoid Motion Generation through ZMP Manipulation based on Inverted Pendulum Control," Proceedings of the 2002 IEEE International Conference on Robotics and Automation, May 2002, Washington, DC, pp. 1404-1409.

Sup, F., "Design and Control of a Powered Transfemoral Prosthesis," The International Journal of Robotics Research, vol. 27, No. 2, Feb. 2008, pp. 263-273.

Taga, G., "A model of the neuro-musculo-skeletal system for human locomotion," Biol. Cybern., vol. 73, No. 2, Jul. 1995, pp. 97-111.

Takayuki "Biped Locomotion using Multiple Link Virtual Inverted Pendulum Model," Publication of Electronics Information and Systems Society, vol. 120, No. 2, Feb. 2000, 8 pages.

Thoroughman, K. and R. Shadmehr, "Learning of action through adaptive combination of motor primitives," Nature, vol. 407, Oct. 2000, pp. 742-747.

Tomovic R. et al., "A Finite State Approach to the Synthesis of Bioengineering Control Systems," IEEE Transations on Human Factors in Electronics, vol. 7, No. 2, Jun. 1966, pp. 65-69.

Tong, et al., "A Practical Gait Analysis System Using Gyroscopes," Medical Engineering & Physics, vol. 21, Mar. 1999, pp. 87-94.

Turker, K., "Electromyography: some methodological problems and issues," Physical Therapy, vol. 73, No. 10, Oct. 1993, pp. 698-710.

van den Bogert, A., "Exotendons for assistance of human locomotion," Biomedical Engineering Online, Oct. 2003, pp. 1-8.

van den Bogert, et al. "A Method for Inverse Dynamic Analysis Using Accelerometry," Journal Biomechanics, vol. 29, No. 7, 1996, pp. 949-954.

Veltink P., et al., "The Feasibility of Posture and Movement Detection by Accelerometry," D-7803-1377-I/93, IEEE, Oct. 1993, pp. 1230-1231.

Vukobratovic M. and Juricic, D., "Contributions to the synthesis of biped gait," IEEE Transactions on Biomedical Engineering, vol. BME-16, No. 1, Jan. 1969, pp. 1-6.

Vukobratovic M. and Stepanenko J., "Mathematical models of general anthropomorphic systems," Mathematical Biosciences, vol. 17, Aug. 1973, pp. 191-242.

Walsh, C., "Biomimetic Design of an Under-Actuated Leg Exoskeleton for Load-Carrying Augmentation," Master's Thesis, MIT, Feb. 2006, pp. 1-94.

Waters, RL., "Energy cost of walking amputees: the influence of level of amputation," J Bone Joint Surg., vol. 58, No. 1, Jan. 1976, pp. 42-46.

Wilkenfeld, A. J., "Biologically inspired auto adaptive control of a knee prosthesis," Ph.D. Thesis, Massachusetts Institute of Technology, Oct. 23, 2000.

Wilkenfeld, A., "An Auto-Adaptive External Knee Prosthesis," Artificial Intelligence Laboratory, MIT, Sep. 2000, Cambridge, MA, pp. 1-3.

Williamson, M., "Series Elastic Actuators," Artificial Intelligence Laboratory, MIT, Jan. 1995, Cambridge, MA, pp. 1-74.

Willemsen A., et al., "Automatic Stance-Swing Phase Detection from Accelerometer Data for Peroneal Nerve Stimulation," IEEE Transactions on Human Factors in Electronics, vol. 37, No. 12, Dec. 1990, pp. 1201-1208.

Willemsen A., et al., "Real-Time Gait Assessment Utilizing a New Way of Accelerometry," Journal of Biomechanics, vol. 23, No. 8, 1990, pp. 859-863.

Williams, B., "Mode Estimation of Model-based Programs: Monitoring Systems with Complex Behavior," Proceedings of the International Joint Conference on Artificial Intelligence, Aug. 2001, Seattle, WA, pp. 1-7.

Winter, D. and Sienko S., "Biomechanics of below-knee amputee gait," Journal of Biomechanics, vol. 21, No. 5, Aug. 1988, pp. 361-367.

Winter, D. A, "Energy generation and absorption at the ankle and knee during fast, natural, and slow cadences," Clinical Orthopedics and Related Research, vol. 175, May 1983, pp. 147-154.

Winter, D, and Robertson D., "Joint torque and energy patterns in normal gait," Biol. Cybem., vol. 29, May 1978, pp. 137-142.

Wisse, M., "Essentails of Dynamic Walking, Analysis and Design of two-legged robots," Phd Thesis, Technical University of Delft, 2004, pp. 1-195.

Woodward et al., "Skeletal Accelerations measured during different Exercises," Proceedings of the Institution of Mechanical Engineers, Part H: Journal of Engineering in Medicine, vol. 207, Jun. 1993, pp. 79-85.

Wu, The Study of Kinematic Transients in Locomotion Using the Integrated Kinematic Sensor, IEEE Transactions on Rehabilitation Engineering, vol. 4, No. 3, Sep. 1996, p. 193-200.

Yakovenko, S., et. al., "Contribution of stretch reflexes to locomotor control: a modeling study," Biol Cybern, vol. 90, No. 2, Jan. 2004, pp. 146-155.

Yun X., "Dynamic state feedback control of constrained robot manipulators," Proc. of the 27th conference on Decision and Control, Dec. 1988, pp. 622-626.

Zlatnik, D., et. al., "Finite-state control of a trans-femoral prosthesis," IEEE Trans. on Control System Technology, vol. 10, No. 3, May 2002, pp. 408-420.

* cited by examiner

ACTIVE ANKLE FOOT ORTHOSIS

CROSS-REFERENCE TO RELATED APPLICATIONS

This application is a continuation of U.S. application Ser. No. 13/299,953, filed on Nov. 18, 2011, which is a continuation of U.S. application Ser. No. 10/671,329, filed on Sep. 25, 2003, now U.S. Pat. No. 8,075,633, and incorporates by reference those applications in their entirety and claims priority thereto.

BACKGROUND OF THE INVENTION

Individuals may suffer from a variety of ankle foot gait pathologies, such as muscle weakness in the anterior and/or posterior compartments of the leg, which severely inhibit locomotory function. For example, drop foot gait is the inability of an individual to lift or dorsiflex their foot because of reduced or no muscular activity, typically in the anterior compartment of the leg around their ankle. The major causes of drop foot include stroke, cerebral palsy, multiple sclerosis, and neurological trauma from accident or surgical complication. The two major complications of drop foot are slapping of the foot after heel strike (foot slap) and dragging of the toe during swing (toe drag). At heel strike, the foot generally falls uncontrolled to the ground, producing a distinctive slapping noise (foot slap). During mid-swing, toe drag prevents proper limb advancement and increases the risk of tripping.

A conventional approach to the treatment of drop foot gait is a mechanical brace called an Ankle Foot Orthosis (AFO), which has increased in popularity over the last several years. Although AFO's offer some biomechanical benefits, disadvantages still remain. For example, AFO's do not improve gait velocity or stride length in children with cerebral palsy. Further, although a constant stiffness AFO is able to provide safe toe clearance in drop foot patients, the device does not reduce the occurrence of slap foot at all walking speeds.

SUMMARY OF THE INVENTION

Increasingly, robotic technology is employed in the treatment of individuals suffering from physical disability, either for the advancement of therapy tools or permanent assistive devices. Initial research has focused primarily on devices that provide therapy to the arms of stroke patients. However, lower extremity robotic devices have recently been developed. When used for permanent assistance, adaptive orthoses enables disabled persons to walk with greater ease and less kinematic difference when compared to normals. Active leg prostheses also show promise. Preliminary studies report that the Otto Bock C-Leg, a microprocessor-controlled artificial knee, provides amputees with an increased independence compared with passive knee prostheses.

In one embodiment, a variable-impedance Active Ankle-Foot Orthosis (AAFO) is provided to treat ankle foot gait pathologies, such as drop foot gait.

Another embodiment for the treatment of ankle foot gait pathologies, such as drop foot gait, includes functional electrical stimulation (FES). Short bursts of electrical pulses can be applied to elicit muscle contractions. FES can be used as a permanent assistance device, and the technology can be customized to the individual using trial-and-error methods and qualitative measurements.

Neither AFOs nor conventional FES systems adapt to the gait of the user, adapt to step-to-step changes in gait pattern due to speed or terrain, or adapt to long-term gait changes due to changes in muscle function. In one embodiment, a computer-controlled Active Ankle Foot Orthosis (AAFO) is provided where joint impedance is varied in response to walking phase and step-to-step gait variations. The AAFO includes an actuator, such as a force-controllable Series Elastic Actuator (SEA) capable of controlling orthotic joint stiffness and damping for plantar and dorsiflexion ankle rotations.

A variable-impedance orthosis has certain clinical benefits for the treatment of drop foot gait compared to both unassisted gait and conventional AFO's that include constant impedance joint behaviors. For example, the major complications of drop foot gait, namely foot slap and toe drag, can be reduced by actively controlling orthotic joint impedance in response to walking phase and step-to-step gait variations. Recent investigations have shown that for the healthy ankle-foot complex, ankle function during controlled plantar flexion closely resembles a linear torsional spring where ankle moment is proportional to ankle position. Thus, by adjusting the stiffness of a virtual linear torsional spring acting about the orthotic joint, forefoot collisions can be minimized and the slap foot complication alleviated, not only at a single speed but at every forward walking speed. Furthermore, during swing, a spring-damper (PD) control can be applied to the orthotic joint, with gains that vary with gait speed, to dorsiflex the ankle through a greater angular range to provide sufficient clearance at variable walking speeds. For individuals suffering from unilateral drop foot gait, changing orthotic joint impedance results in a more symmetric gait between affected and unaffected legs.

BRIEF DESCRIPTION OF THE DRAWINGS

The foregoing and other objects, features and advantages of the invention will be apparent from the following more particular description of various embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of various embodiments of the invention follows.

Figure 1:
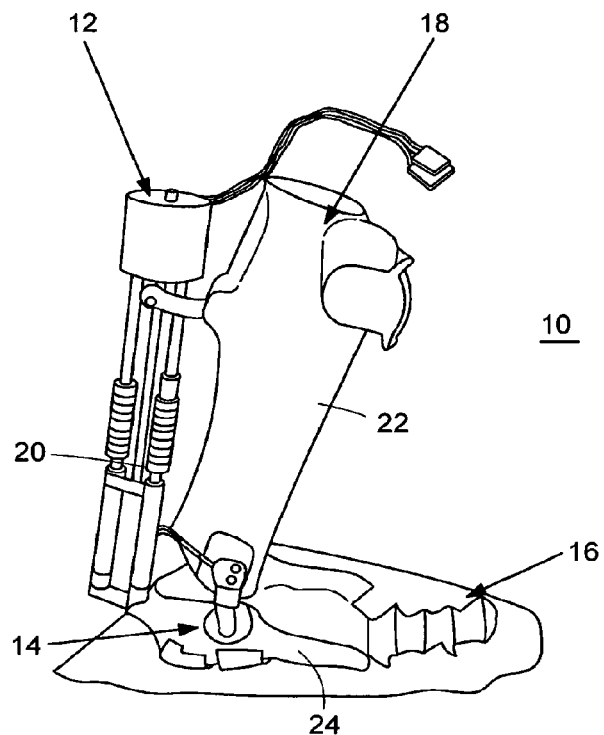
FIG. 1 is a side view of an embodiment of an Active Foot Orthosis (AAFO).

FIG. 1 illustrates an embodiment of an AAFO 10, an actuator 12, and sensors 14, 16 attached to a conventional AFO 18. In one embodiment, the AAFO 10 has a total weight of about 2.6 kg, excluding the weight of an off-board power supply. In a particular embodiment, the actuator 12 includes a Series Elastic Actuator (SEA), previously developed for legged robots, for controlling the impedance of the orthotic ankle joint for sagittal plane rotations. The SEA 12 can include a brushless DC motor in series with a spring. The SEA 12 provides force control by controlling the extent to which the series spring 20 is compressed. The deflection of the spring 20 can be measured by a linear potentiometer sampled at 1000 Hz and passed through a first order filter with a cutoff frequency equal to 50 Hz. The signal can be numerically differentiated and passed through another first order filter with a cutoff frequency of 8 Hz. The deflection of the series spring 20 can be controlled using a proportional-derivative (PD) controller.

Some advantages of the SEA 12 are that it has low impedance, the motor is isolated from shock loads, and the effects of backlash, torque ripple, and friction are filtered by the spring 20. A further advantage is that the SEA 12 exhibits stable behavior while in contact with most environments, even when in parallel with a human limb. In particular embodiments, the SEA 12 allows for the implementation of any virtual, torsion mechanical element about the ankle.

In a particular embodiment, the conventional AFO 18 includes a standard polypropylene AFO with a metallic hinge, such as a Scotty© ankle joint. This joint allows free motion in the sagittal plane (plantar and dorsiflexion) but is rigid for inversion/eversion movements. The AFO 18 can be modified by molding two recesses—one at the heel and the other at mid-calf. Several holes can be drilled in these recesses to attach the SEA 12.

In a particular embodiment, an ankle angle sensor 14 includes a Bourns 6637S-1-502 5 k$\Omega$ rotary potentiometer to determine the angle between a shank or leg portion 22, which is attachable to a person's foot, and the foot 24. The angle sensory signal can be sampled at 1000 Hz and passed through a first order low pass filter with a cutoff frequency of 50 Hz. The ankle velocity can be found by differentiating the pot signal and then passing it through a second order Butterworth filter with a cutoff frequency of 8 Hz. In another embodiment, the position of the orthotic ankle joint can be measured with a rotary encoder placed on the SEA 12. Such a sensor can measure motor position directly and orthotic position indirectly.

In other embodiments, Ground Reaction Force (GRF) sensors 16 can be used to measure forces on the foot 24. In a particular embodiment, an Ultraflex system can be used. In one embodiment, six capacitive force transducers, 25 mm square and 3 mm thick, can be placed on the bottom or foot 24 of the AFO 18, two sensors beneath the heel and four beneath the forefoot region. In particular embodiments, each sensor 16 can detect up to 1000 N, and can have a resolution of 2.5, and a scanning frequency of 125 Hz. The signal from each sensor 16 can be passed through a first-order filter with a cut-off frequency equal to 5 Hz. A single foot switch, model MA-153, can be placed in the heel of a shoe worn with the orthosis to detect heel strike approximately 30 ms earlier than the Ultraflex force sensors.

Ankle biomechanics for level ground walking on smooth surfaces can be described using four distinct walking phases. In this description, only sagittal rotations are described, that is to say, dorsi and plantarflexion and not inversion-eversion movements.

Beginning with heel strike, the stance ankle begins to plantarflex slightly. This flexion, called controlled plantarflexion, allows for a smooth heel-strike to forefoot-strike transition. Recent investigations show that the torque versus angle data are spring-like with ankle torque increasing linearly with ankle position. Although a normal, healthy ankle behaves as a passive mechanical linear spring within a contact phase, the stiffness of that linear spring is continually modulated by the central nervous system from step to step. It is believed that the body adjusts ankle spring stiffness to achieve a fixed energy absorption and release at each walking speed. Data also show that energy absorption and release increases with increasing walking speed, necessitating an increase in ankle stiffness with walking speed (when the heel-strike angle remains invariant to speed variations).

After maximum plantarflexion is reached in the stance ankle, the joint begins to dorsiflex. In this particular walking phase, called controlled dorsiflexion, the ankle also is spring-like but is distinctly nonlinear; here, ankle stiffness increases with increasing ankle dorsiflexion to gradually slow tibia progression.

During late stance, the ankle begins to power plantarflex to drive kinetic energy into the lower limb in preparation for the swing phase. For moderate to fast walking speeds, about 10-20 Joules of ankle work are performed. That energy is above and beyond the spring energies stored and released from early to late stance.

As the hip is flexed, and the knee has reached a certain angle in knee break, the leg leaves the ground and the knee continues to flex. Throughout the swing phase, the swing foot continues to rotate to cancel the angular momentum of the adjacent stance foot such that the net angular momentum contribution about the body's center of mass is zero.

Figure 2:
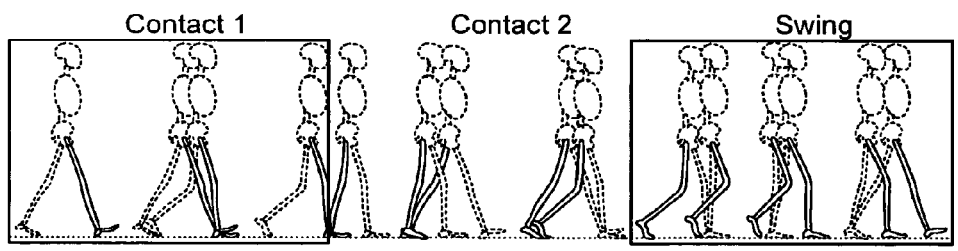
FIG. 2 illustrates individual states for a finite machine.

A finite state machine can be implemented to address each complication of an ankle foot gait pathology, such as drop foot gait. Three states were used, each with a specific control objective (FIG. 2). Contact 1 spans the first half of ground contact from heel strike to the middle of mid-stance when the tibia first becomes perpendicular with the foot. Contact 2 spans the second half of ground contact, beginning when the tibia first becomes perpendicular with the foot and ending at toe-off when the leg first loses contact with the ground. Finally, the Swing state spans the entire swing phase, from toe-off to heel strike.

Figure 3:
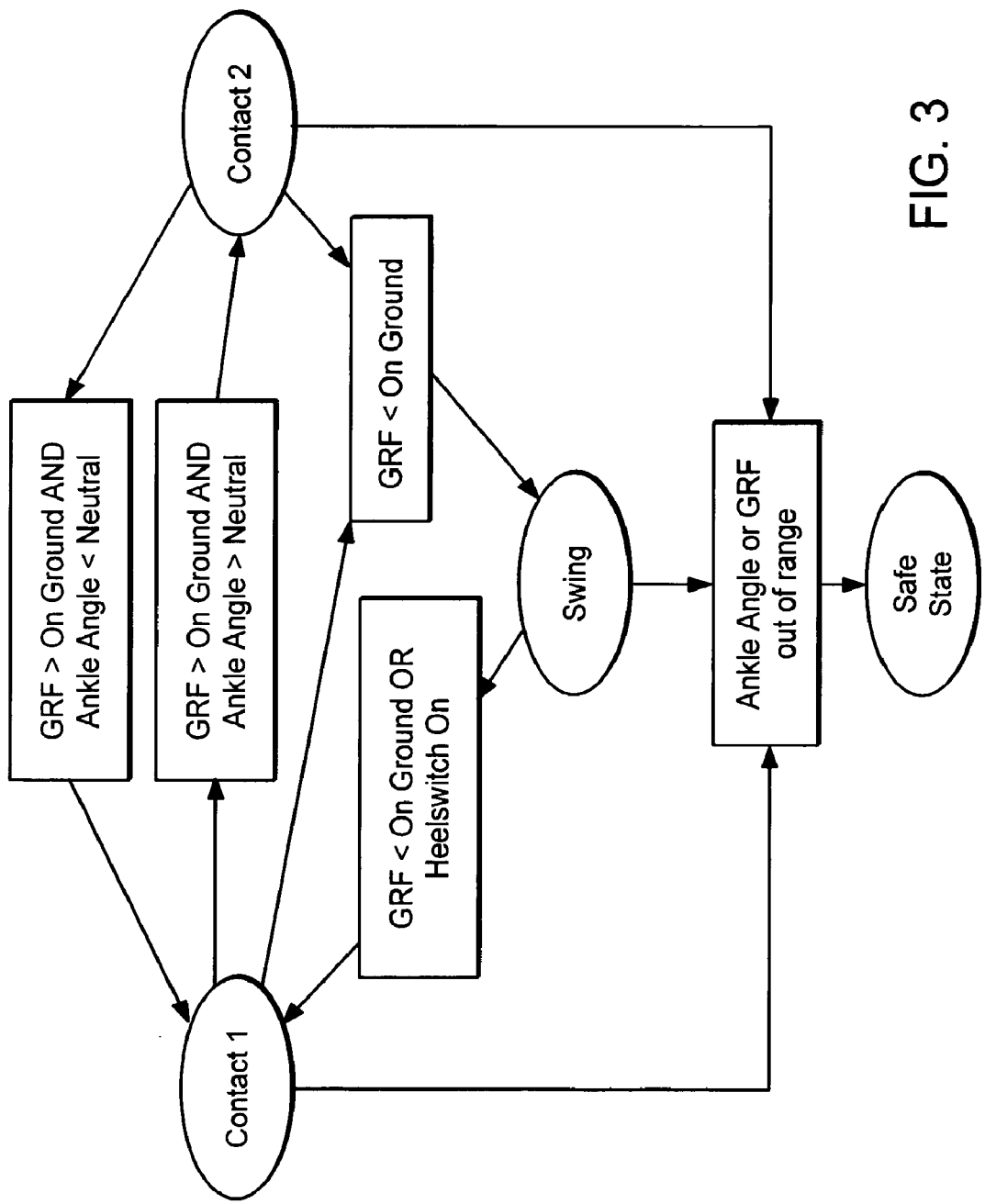
FIG. 3 illustrates triggers for the finite machine of FIG. 2.

In a Contact 1 state, from heel strike to midstance, the objective of the controller is to prevent foot slap. During a Contact 2 state, from midstance to toe-off, the controller minimizes the impedance of the brace so as not to impede power plantar flexion movements. Finally, in a Swing state, spanning the entire swing phase, the user's foot is lifted to prevent toe drag. A Safe State can be used to shut off the device when any unexpected circumstances occur. The triggers or transitional parameters for the finite state machine are shown in FIG. 3.

For a gait cycle in accordance with one embodiment, Contact 1 begins when the foot switch within the heel was compressed. In this embodiment, the transition into Contact 2 occurred when the Ground Reaction Force (GRF), equal to the sum of all six force transducers, was greater than On Ground, equal to about 60 N, and when the ankle was in dorsiflexion. The ankle was considered to be in dorsiflexion when the angle between the tibia and foot was less than 90°. In this embodiment, On Ground was set to about 60 N because this particular value reliably discerned ground contact from noise during swing. Contact 2 ended when the GRF was less than On Ground. In fact, the transition into Swing always occurred when the GRF was less than On Ground. The controller transitioned to the Safe State when any of the force or angle sensory signals went beyond a specified normal operating range. In this embodiment, the range for each force sensor was about 1000 N, the maximum force that any one sensor should measure in walking for a 90 kg person. The acceptable range for the angle sensor was about ±45 degrees, the normal operating range for the human ankle.

During controlled plantar flexion (CP), normal ankle function can be modeled as a linear rotational spring where ankle moment is proportional to ankle position. Thus, during the CP phase of walking, a linear torsional spring control can be used for the orthotic ankle joint. As a criterion for selecting a desired stiffness of the orthotic torsional spring, the controller can be used to analyze the ground reaction force generated at the moment of forefoot impact after each walking step. The extent of foot slap can be deemed too extreme, and the CP stiffness too low, if a high frequency force spike occurs at the moment of forefoot collision.

Figure 4B:
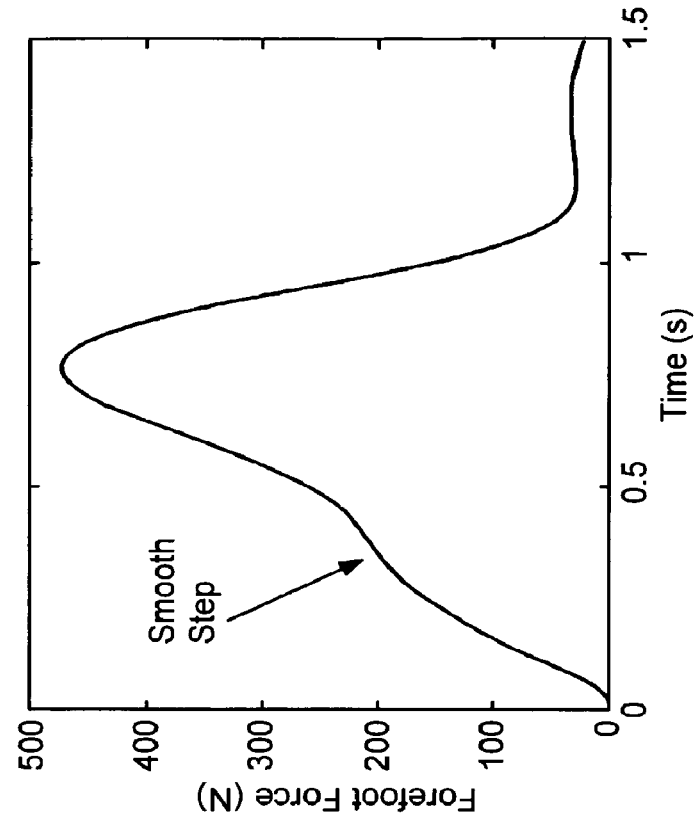
FIG. 4B is a representative forefoot ground reaction force from a normal participant.
Figure 4A:
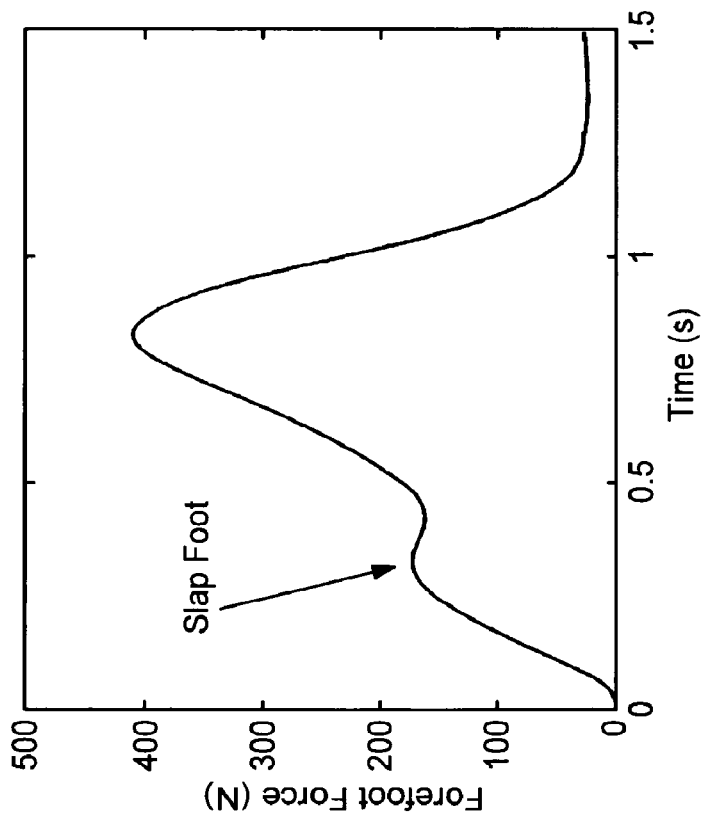
FIG. 4A is a representative forefoot ground reaction force from a drop foot participant.

In FIGS. 4A and 4B, a representative forefoot force signal from a drop foot participant is compared to a forefoot force signal from a normal participant. Both participants wore the AAFO 10 under a zero impedance control, and the forefoot force signal was computed from the sum of all four force transducer signals measured in the forefoot region. In FIG. 4A, a dual peak force pattern indicates the occurrence of foot slap in the drop foot participant, whereas in FIG. 4B, the lack of a dual force spike indicates that no foot slap had occurred in the normal participant.

To detect the dual peaks and the occurrence of foot slap, the AAFO controller can numerically differentiate the forefoot force and then filter that signal using a second order Butterworth filter with a cutoff frequency of about 0.6 Hz. If substantial foot slap occurs, the differential of the forefoot force is negative, and the stiffness of the orthotic torsional spring stiffness can be incremented. The CP stiffness can be started at zero and incremented by the rules shown in Table I, where the incremental stiffness (SF) was 5.7 Nm/rad (0.1 Nm/deg), approximately 2% of the anticipated final ankle stiffness.

TABLE I

| Number of slaps in last 5 steps (n) | Change in Ankle Stiffness |
|---|---|
| 0 | −ΔΓ |
| 1 | 0 |
| 2-5 | (n-1) ΔΓ |

Gait speed is an important step-to-step gait variation for which the AAFO 10 can respond and adapt. In a particular embodiment, the time of foot contact, defined as the time that a foot remains in contact with the ground from heel strike to toe-off, can be used as a measure of forward speed. With an expectation that orthotic CP stiffness should change with gait speed, the full range of gait contact times can be divided into bins, denoting velocity ranges. During each swing phase, stance time can be estimated from the orthotic force transducers 16, and the participant's time of contact bin, or forward speed range, can be selected. Within each bin, the AAFO controller can optimize the orthotic CP stiffness. In one embodiment, only three bins are necessary to span the full speed range of the participants.

Drop foot participants typically do not experience any difficulties during powered plantar flexion. Hence, the control objective of Contact 2 is to minimize orthotic joint impedance so as not to impede the participants' power plantar flexion movements. During this state, the SEA's 12 target force can be set to zero.

During the swing phase, a second-order, under-damped mechanical model (spring-damper PD control), previously used to characterize normal ankle function, can be used to control the orthotic ankle joint. Using the AAFO 10, each drop foot participant can walk at slow, self-selected, and fast speeds, and the swing phase ankle angle can be collected on both the affected and unaffected sides. At each speed, orthotic joint stiffness can be increased manually until the early swing phase dorsiflexion velocity measured on the affected side matched the unaffected side. Orthotic joint damping can be increased from zero until unwanted joint oscillations are removed. The final values of stiffness and damping in this particular embodiment are listed in Table II below.

TABLE II

| Gait Speed | K (Nm/rad) | B (Nms/rad) |
|---|---|---|
| Slow | 28.65 | 0.57 |
| Normal | 37.24 | 1.03 |
| Fast | 45.84 | 1.15 |

The stiffness and damping values for the drop foot users are not correlated with gait speed directly, but with ranges of stance time, in the same manner to the CP stiffness control described earlier.

Example

A clinical evaluation of the AAFO 10 was conducted in the Gait Laboratory at Spaulding Rehabilitation Hospital, Boston, Mass. Drop foot participants having only a unilateral drop foot condition were selected, and on their affected side, participants did not suffer from a gait disability other than drop foot. Both participants had an absence of strongly manifesting spasms and contractures in lower extremity joints. Finally, each participant had used an AFO for at least two years and therefore was experienced at AFO ambulation. Subjects reached a stable neurological state after the incident that caused their disability. Thus, no recovery of function was expected or found. Three normal subjects were matched for gender, height, weight, and age to the drop foot participants. Subject sex, age, mass, height, and self-selected gait speed are listed in Table III.

TABLE III

| Subject | Sex | Age (yr) | Mass (kg) | Height (m) | Self-Selected Gait Speed (m/s) |
|---|---|---|---|---|---|
| Drop Foot | M | 62 | 79.1 | 1.79 | 1.22 |
| Drop Foot | M | 62 | 95.4 | 1.77 | 1.07 |
| Normal | M | 66 | 76.6 | 1.70 | 1.39 |
| Normal | M | 67 | 86.1 | 1.75 | 1.01 |
| Normal | M | 67 | 73.2 | 1.70 | 1.22 |

Kinematic and kinetic data were measured on both the affected and unaffected sides using an eight-camera VICON 512 system and two AMTI force plates. The data were processed at 120 Hz with VICON Workstation using the standard model of the lower limbs included with the software. These data were then analyzed using MATLAB.

The subjects donned the AAFO in three different control conditions: zero, constant, and variable impedance. The zero impedance control setup was implemented by setting the target force on the SEA to zero, thereby minimizing the impedance contribution of the orthosis across the ankle joint. This setup was meant to approximate unassisted drop foot gait. For the constant impedance control setup, the AAFO controller commanded a constant joint stiffness, independent of walking phase and gait speed. This joint stiffness was the converged controlled plantar flexion (CP) stiffness from the variable impedance control that minimized the number of slap foot occurrences at the self-selected gait speed. This constant impedance control condition was designed to imitate conventional AFO technology employed in the treatment of drop foot gait.

For each controller, subjects walked at slow, self-selected, and fast gait speeds. The subjects first walked at their self-selected speed using the constant impedance control setup. The amount of time required to cover a specified distance was measured using a stopwatch. Subjects were then asked to reduce their time by 25% for the fast gait speed and increase their time by 25% for the slow gait speed. These times were then matched when testing the remaining two control conditions.

A stride cycle was defined as the period of time for two steps, and was measured from the initial heel contact of one foot to the next initial heel contact of the same foot. All data were time normalized to 100% of the stride cycle. The ankle angle data during a gait cycle were fitted with a cubic spline function and then resampled to 200 samples so that each point was 0.5% of the gait cycle.

In this study, it was assumed that normal gait was symmetrical and that deviations from a reference pattern were a sign of disability. To analyze spatial asymmetry, the step length on the affected side ($L_{affected}$) was subtracted from the step length on the unaffected side ($L_{unaffected}$). The difference in stride lengths ($L_{sym}$) should be zero for symmetric gait:

$$L_{sym} = L_{affected} - L_{unaffected} \quad (1)$$

To analyze temporal asymmetry, the step time on the affected side ($T_{affected}$) was subtracted from the step time on the unaffected side ($T_{unaffected}$). The difference in stride times ($T_{sym}$) should be zero for symmetric gait:

$$T_{sym} = T_{affected} - T_{unaffected} \quad (2)$$

A multiple comparison using a one-way analysis of variance (ANOVA) was used to determine which means were significantly different for the gait symmetry. P values less than 0.05 were considered significant for all tests.

Figure 5:
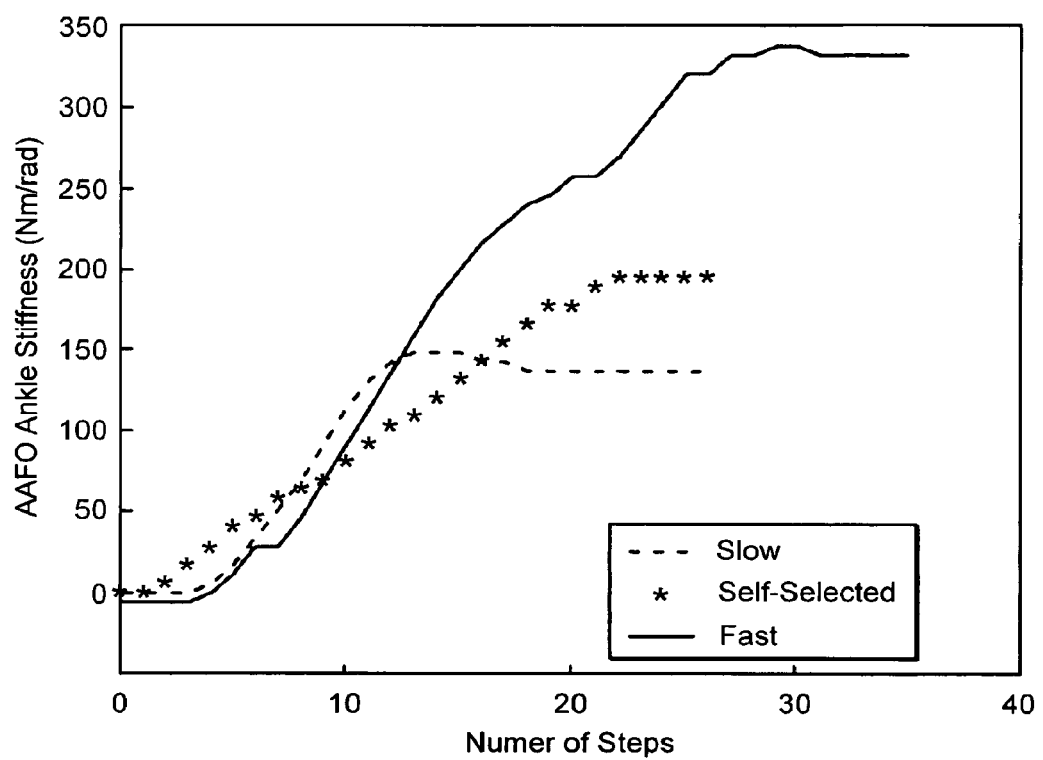
FIG. 5 illustrates orthotic joint stiffness plotted against the number of steps taken by a participant starting from an initial default impedance value of zero.

The first evaluation of the drop foot controller was to test whether the system was capable of converging to a final CP stiffness that reduced or prevented slap foot. For each of the three gait speeds, the controller was able to converge to a final stiffness value within 32 steps (FIG. 5). The CP stiffness increases with increasing gait speed. During the stiffness convergence at each of the three gait speeds, the occurrences of the high frequency forefoot force signal (typical of slap foot; see FIG. 4A) were reduced.

Figure 6:
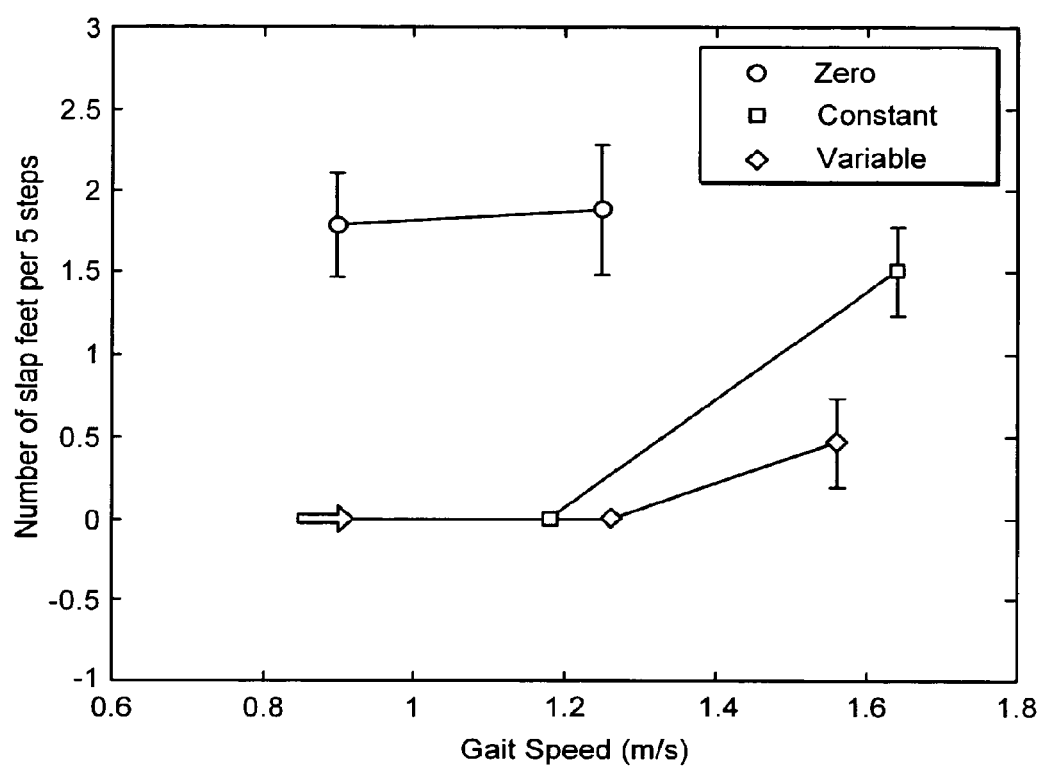
FIG. 6 illustrates slap foot occurrences per 5 steps (n=5) measured on two drop foot subjects walking at slow, self-selected, and fast speeds.

As a measure of the slap foot complication, the average number of occurrences of slap foot per 5 steps (25 steps total) were calculated for each drop foot subject, control condition, and gait speed (n=5). The participants were unable to walk at the fast gait speed using the zero force condition because it was not deemed safe. The constant impedance condition eliminated the occurrences of slap foot at the slow and self-selected gait speeds (FIG. 6). The three curves correspond to zero, constant, and variable impedance control conditions. However, slap foot occurrences increased at the fast gait speed. By adjusting CP stiffness with gait speed in the variable-impedance control condition, the number of occurrences of slap foot was reduced at the fast gait speed by 67% compared to the constant stiffness condition.

Figure 7:
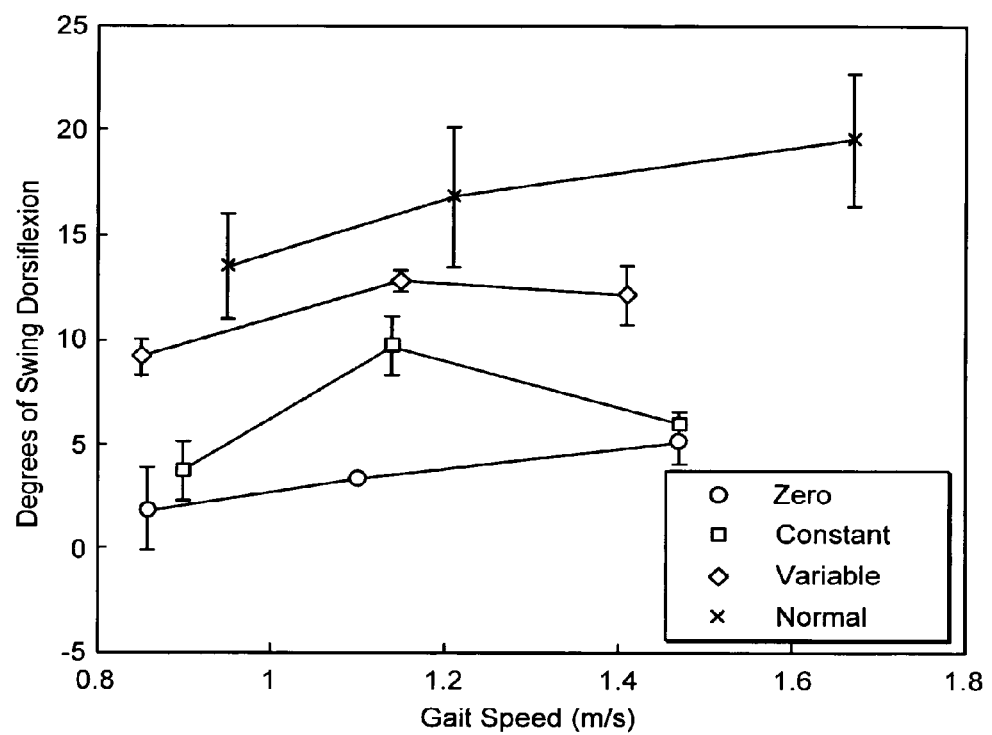
FIG. 7 is a plot of the amount of swing dorsiflexion for normal (n=3) and drop foot (n=2) participants.

To quantify the reduction of the second major complication of drop foot, or toe drag, the swing dorsiflexion angular range was used. The dorsiflexion angular range was defined as the maximum plantar flexion angle during the powered plantar flexion phase of stance minus the maximum dorsiflexion angle during swing. The variable impedance control was able to increase the amount of swing dorsiflexion as compared to the constant impedance condition by 200%, 37%, and 108% for slow, self-selected, and fast gait speeds, respectively (FIG. 7). All data points for the normal participants are an average of 15 trials, whereas for the drop foot participants the averages are over 20 trials.

Figure 8:
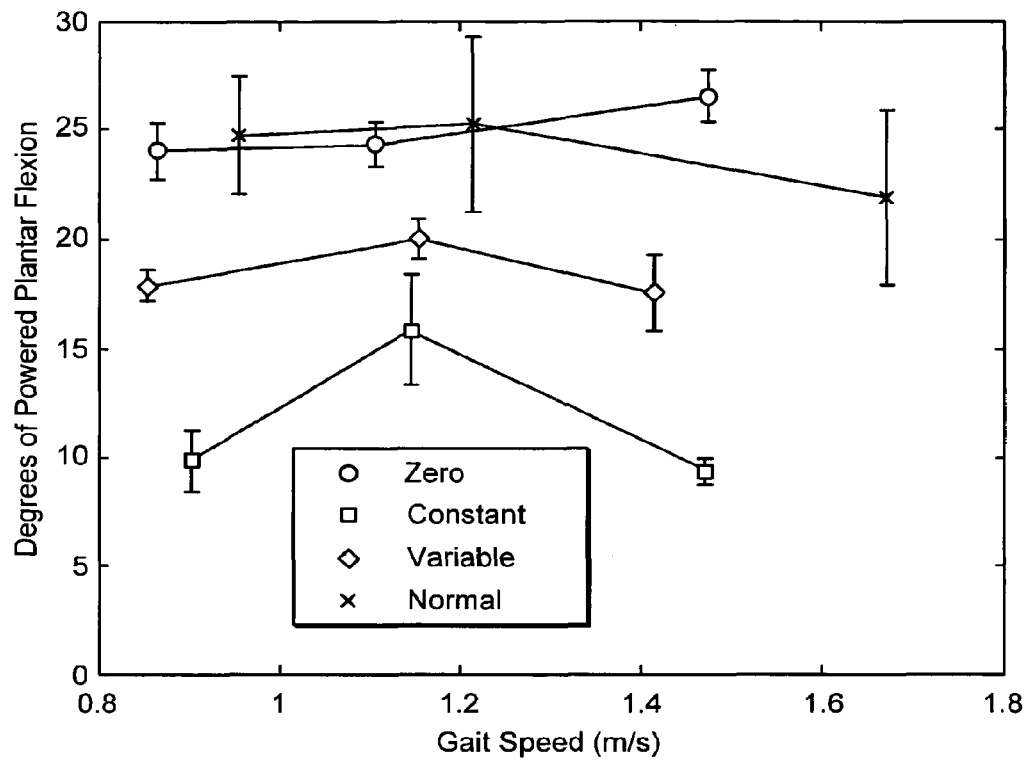
FIG. 8 illustrates the amount of powered plantar flexion for normal (n=3) and drop foot (n=2) participants.

A constant impedance ankle-foot orthosis hinders powered plantar flexion (PP) since a dorsiflexion moment will be exerted against the foot during late stance. As expected, the constant impedance condition reduced the PP angle as compared to the zero impedance condition and the normals (FIG. 8). Here the PP angle was defined as the maximum plantar flexion angle during power plantar flexion minus the maximum dorsiflexion angle during controlled dorsiflexion in stance. The variable-impedance controller had a larger PP angle than the constant impedance control condition by 89%, 25%, and 82% for the slow, self-selected, and fast gait speeds, respectively.

To evaluate spatial and temporal gait symmetry, the differences in step lengths ($L_{sym}$) (m) and step times ($T_{sym}$) (s) from the affected to the unaffected side were compared for each of the three control conditions (n=20). The results are set forth in Table IV below.

TABLE IV

|  | $L_{sym}$(m) | | $T_{sym}$(s) | |
| --- | --- | --- | --- | --- |
|  | Self-selected | Slow | Self-selected | Slow |
| Zero Impedance | 0.08 ± 0.07 | 0.09 ± 0.09 | 0.09 ± 0.07 | 0.15 ± 0.16 |
| Constant Impedance | 0.04 ± 0.06 | 0.02 ± 0.08 | 0.07 ± 0.05 | 0.04 ± 0.12 |
| Variable Impedance | 0.02 ± 0.07 | 0.00 ± 0.07 | 0.02 ± 0.09 | 0.01 ± 0.16 |

Both $L_{sym}$ and $T_{sym}$ for the variable-impedance controller were significantly smaller than the zero impedance controller for both the self-selected and slow gait speeds (p<0.05). The zero and constant impedance conditions were significantly different for the slow gait speed (p<0.05). For the fast gait speed, a comparison was not possible because the step length for both sides could not be calculated for a single walking cycle.

An active ankle foot orthosis is provided in accordance with aspects of the present invention. Zero, constant, and variable-impedance control strategies were evaluated on two persons suffering from unilateral drop foot gait. It was found that actively adjusting joint impedance in response to walking phase and forward speed reduces the occurrence of slap foot, and provides for swing phase ankle kinematics more closely resembling normals as compared to the zero and constant impedance control schemes. Furthermore, it was found that a variable-impedance control allows for greater powered plantar flexion compared to a conventional constant stiffness approach where a dorsiflexion spring impedes powered plantar flexion movements during late stance.

Although the major complications of drop foot are reduced with a variable-impedance control, the findings do not support the hypothesis that changing orthotic joint impedance will result in a more symmetric gait between affected and unaffected legs in unilateral drop foot gait. To test the hypothesis, spatial and temporal gait symmetry was evaluated according to the difference in step lengths and times between affected and unaffected sides. When using the variable-impedance control, the difference in step time and step length was not significantly different from that measured with the constant impedance control condition. However, for both gait speeds analyzed, the variable-impedance controller did improve spatial and temporal gait symmetry compared to the zero impedance control condition, whereas the constant impedance control did not.

The CP stiffness was optimized within each gait speed range, or time of contact bin. After the variable-impedance controller adapted CP stiffness across gait speed, the final stiffness at the slow speed was 36% less, and at the fast speed, 57% greater than at the self-selected speed. Thus, from slow to fast speeds, stiffness increased more than two-fold. A constant stiffness spring tuned only to the self-selected speed allowed slap foot to occur at fast walking speeds (FIG. 6). It also made the ankle too stiff during slow walking, reducing the angular rotation of the ankle during controlled plantar flexion movements in early stance.

The primary concern for both the drop foot participants in the study was catching their toe during swing and losing their balance. With constant swing phase impedance, both users caught their toe at the fast gait speed. This was not surprising given the fact that, for normal gait, the amount of time to lift the foot and achieve toe clearance was found to decrease by a factor of two from slow to fast speeds. To achieve this time decrease with the AAFO 10, a four-fold increase in swing joint stiffness was necessary (Table II). Thus, changing orthotic joint impedance with gait speed, in order to lift the toe during swing, appears to be a desired control feature of the variable-impedance AAFO 10.

Normal ankle function has been modeled as a linear spring during controlled plantar flexion, and as a non-linear, stiffening spring during controlled dorsiflexion. Throughout the swing phase, the ankle has been represented by a linear torsional spring and damper. Given these differences in ankle function within a single gait cycle, an assistive ankle device, acting in parallel with the human ankle-foot complex, should ideally change its impedance in response to walking phase. To this end, a state controller was used in the AAFO 10, and joint impedance was modulated in response to walking phase.

During the controlled plantar flexion phase of walking, or Contact 1, a linear torsional spring control was employed where the stiffness was adjusted to prevent slap foot. From mid-stance to pre-swing, or the Contact 2 state, a zero impedance control was implemented so as not to impede normal powered plantar flexion movements. Finally, during the Swing state, a spring-damper PD control was implemented to provide toe clearance. The primary difficulty with the constant impedance control was the reduction of powered plantar flexion movements (FIG. 8). All data points for the normal participants are an average of 15 trials, whereas for the drop foot participants the average is over 20 trials. Here the spring-damper control used to prevent toe drag was acting against the foot when the users attempted to plantar flex their ankle during late stance.

The variable-impedance controller should have a similar maximum power plantarflexion angle as the zero impedance condition since both controllers were designed to not impede late stance power plantarflexion movements. However, this behavior was not observed (FIG. 8). It was discovered that the variable-impedance controller transitioned into the Swing state too early, before the foot actually left the ground, due to a lack of resolution in the forefoot force sensors. Consequently, the Swing spring-damper controller was activated too early, impeding power plantarflexion movements during late stance. In other embodiments, a foot switch can be positioned in the forefoot region to more accurately detect the event of toe-off.

In alternative embodiments, FES can be used to treat ankle foot gait pathologies, including drop foot gait. Instead of using a synthetic motor to vary ankle impedance, the muscles of the patient can be electrically stimulated to achieve desired ankle impedances as described herein. That is, a FES controller can be used to actively modulate ankle impedance to achieve a linear torsional spring during controlled plantar flexion to minimize forefoot collisions with the ground, minimize impedance during late stance, and achieve a spring-damper during a swing phase. Recent theoretical and experimental investigations have found that a positive force feedback FES control results in robust, spring-like muscle operations. Hence, for the stance phases of walking where a spring-like response is desired, a positive force feedback strategy can be employed. Here muscle or tendon force is the feedback sensory signal. The greater the force borne by the muscle-tendon unit, the greater is the muscle activation. This approach is not only robust to variations in muscle force-length and force-velocity curves, but is a control that rejects system energy disturbances as an emergent response.

While this invention has been particularly shown and described with references to various embodiments thereof including treatment of drop foot gait, it will be understood by those skilled in the art that various changes in form and details may be made therein without departing from the scope of the invention encompassed by the appended claims. For example, the devices and methods can be used to treat a variety of ankle foot gait pathologies, including patients suffering from anterior and/or posterior muscle weakness(es).

What is claimed is:

1. A method for operating an autonomous motorized permanent assistance leg device, the method comprising the steps of:
    measuring an amount of time a foot is in contact with ground;
    estimating a forward speed based on the ground contact time; and
    modulating an impedance of the device based at least in part thereon.

2. The method of claim 1, wherein the measuring step comprises using a sensor comprising at least one of a ground reaction force sensor and a foot sensor, wherein the foot sensor is disposed in at least one of a forefoot region and a heel region.

3. The method of claim 1, wherein the modulating step comprises actuating a series elastic actuator.

4. The method of claim 3, wherein the series elastic actuator comprises a motor in series with a spring.

5. The method of claim 4, wherein actuating the series elastic actuator comprises controlling compression of the spring.

6. The method of claim 1, wherein the impedance modulating step is based at least in part on step-to-step gait variations.

7. The method of claim 1, wherein the impedance modulating step is based at least in part on the forward speed to lift a toe during a swing phase.

8. The method of claim 7, wherein the toe is lifted to provide toe clearance to reduce toe drag during the swing phase.

9. The method of claim 7, wherein the impedance modulating step controls ankle movement during controlled plantar flexion.

10. The method of claim 9, wherein ankle movement is controlled to reduce foot slap during a stance phase.

11. The method of claim 1, wherein the leg device comprises an ankle orthosis comprising an ankle joint, and the method further comprises the step of controlling plantar flexion and dorsiflexion of ankle joint position during at least a stance phase.

12. The method of claim 1, wherein the device comprises an ankle device.

13. The method of claim 12, wherein the modulating step comprises adjusting ankle stiffness.

14. A method for controlling an autonomous motorized permanent assistance ankle device comprising a foot, a leg portion and an actuator, the method comprising the steps of:
- monitoring, with at least one sensor, at least one of position and movement of the ankle device throughout at least one gait cycle;
- determining at least one characteristic of the gait cycle; and
- adjusting the device based on the determined characteristic by controlling the actuator to affect movement of the leg portion relative to the foot.

15. The method of claim 14, wherein the adjusting step comprises using information from the at least one sensor to dorsiflex the foot relative to the leg portion during a swing phase.

16. The method of claim 14, wherein adjusting the ankle comprises dorsiflexing and plantarflexing the ankle.

17. The method of claim 16, wherein during a swing phase of a gait cycle, the ankle is first dorsiflexed then plantarflexed during the swing phase.

18. The method of claim 17, wherein during the swing phase the ankle is first moved to a dorsiflexed position then moved to a plantarflexed position.

19. The method of claim 14, wherein the method is adapted to characterize normal ankle function.

20. The method of claim 19, wherein the ankle in a swing phase follows a substantially second-order mechanical model.

21. The method of claim 20, wherein the ankle in the swing phase follows a substantially underdamped mechanical model.

22. A method for operating an autonomous motorized permanent assistance leg device, the method comprising the steps of:
- monitoring, with at least one sensor, a parameter associated with use of the device;
- using information from the sensor to determine a phase of a gait cycle; and
- using a motor to adjust an ankle angle of the device based on the phase of the gait cycle by dorsiflexing the ankle angle during a swing phase.

23. The method of claim 22, wherein dorsiflexing the ankle angle provides toe clearance.

24. The method of claim 22, wherein the adjustment step is a function of gait speed.

* * * * *